US011571454B2

(12) United States Patent
Medina et al.

(10) Patent No.: US 11,571,454 B2
(45) Date of Patent: *Feb. 7, 2023

(54) ANTICANCER PEPTIDES THAT SYNERGISTICALLY ENHANCE CHEMOTHERAPEUTIC POTENCY

(71) Applicant: The Penn State Research Foundation, University Park, PA (US)

(72) Inventors: Scott Hammond Medina, State College, PA (US); Andrew William Simonson, Kennett Square, PA (US); Matthew Aronson, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/181,914

(22) Filed: Feb. 22, 2021

(65) Prior Publication Data

US 2021/0177931 A1    Jun. 17, 2021

Related U.S. Application Data

(63) Continuation-in-part of application No. 16/619,490, filed as application No. PCT/US2018/035942 on Jun. 5, 2018, now Pat. No. 11,458,099.

(60) Provisional application No. 62/979,897, filed on Feb. 21, 2020, provisional application No. 62/515,019, filed on Jun. 5, 2017.

(51) Int. Cl.
*A61K 38/10*    (2006.01)
*A61P 35/00*    (2006.01)
*A61K 38/17*    (2006.01)
*A61K 45/06*    (2006.01)

(52) U.S. Cl.
CPC ............ *A61K 38/10* (2013.01); *A61K 45/06* (2013.01); *A61P 35/00* (2018.01)

(58) Field of Classification Search
None
See application file for complete search history.

(56) References Cited

U.S. PATENT DOCUMENTS

| 5,811,124 A | 9/1998 | Fernandez et al. |
| 6,884,435 B1 | 4/2005 | O'Hagan et al. |
| 7,329,638 B2 | 2/2008 | Yang et al. |
| 8,343,475 B2 | 1/2013 | Hancock et al. |

FOREIGN PATENT DOCUMENTS

| KR | 101096679 B1 | 12/2011 |

OTHER PUBLICATIONS

Manca et al., "Fabrication of polyelectrolyte multilayered vesicles as inhalable dry powder for lung administration of rifampicin," International Journal of Pharmaceutics, 2014, vol. 472, pp. 102-109.
Palena et al., "Self-organized nanoparticles based on drug-interpolyelectrolyte complexes as drug carriers," J Nanopart Res, 2012, vol. 14, No. 867, 12 pages.
Silva et al., "Delivery of LLKKK18 loaded into self-assembling hyaluronic acid nanogel for tuberculosis treatment," Journal of Controlled Release, 2016, vol. 235, pp. 112-124.
USPTO, Office Action for U.S. Appl. No. 16/619,490, dated Jan. 7, 2022.
Ramadoss et al., "Small molecule inhibitors of trans-translation have broad-spectrum antibiotic activity," PNAS, 2013, vol. 110, No. 25, pp. 10282-10287.
Ramon-Garcia et al., "Targeting *Mycobacterium tuberculosis* and Other Microbial Pathogens Using Improved Synthetic Antibacterial Peptides," Antimicrobial Agents and Chemotherapy, 2013, vol. 57, No. 5, pp. 2295-2303.
Zamani et al., "Advances in drug delivery via electrospun and electrosprayed nanomaterials," International Journal of Nanomedicine, 2013, vol. 8, pp. 2997-3017.
Brown, Kelly L. et al, "Cationic host defense (antimicrobial) peptides", Current Opinion in Immunology, Feb. 2006, pp. 24-30, vol. 18, issue 1.
Hancock, Robert E.W. et al, "Antimicrobial and host-defense peptides as new anti-infective therapeutic strategies", Nature Biotechnology, Dec. 11, 2006, pp. 1551-1557, vol. 24.
Lankalapalli, Srinivas et al, "Polyelectrolyte Complexes: A Review of their Applicability in Drug Delivery Technology", Indian journal of pharmaceutical sciences, Sep. 2009, pp. 481-487, vol. 71, issue 5.
Fjell, Christopher D. et al, "Designing antimicrobial peptides: form follows function", Nature Reviews Drug Discovery, Dec. 16, 2011, pp. 37-51, vol. 11.
Lankalapalli, Srinivas et al, "Preparation and evaluation of vancomycin polyelectrolyte complex nanoparticles." Indian Journal of Nanoscience, Aug. 1, 2014, pp. 10-18, vol. 2, issue 8.
Palena, Maria Celeste et al, "Self-organized drug-interpolyelectrolyte nanocomplexes loaded with anionic drugs. Characterization and in vitro release evaluation", Journal of Drug Delivery Science and Technology, Dec. 2015, pp. 45-53, vol. 30.
Abedinzadeh, Maria et al, "Natural antimicrobial peptides against *Mycobacterium tuberculosis*", Journal of Antimicrobial Chemotherapy, Feb. 12, 2015, pp. 1285-1289, vol. 70, Issue 5.
Water, Jorrit J. et al, "Hyaluronic Acid-Based Nanogels Produced by Microfluidics-Facilitated Self-Assembly Improves the Safety Profile of the Cationic Host Defense Peptide Novicidin", Pharmaceutical Research, Mar. 27, 2015, pp. 2727-2735, vol. 32.

(Continued)

*Primary Examiner* — Bethany P Barham
*Assistant Examiner* — Peter Anthopolos
(74) *Attorney, Agent, or Firm* — Hodgson Russ LLP

(57) ABSTRACT

Provided is a method for treating cancer by administering to an individual who has the cancer a MAD1 peptide. The peptide can enhance the effect of a chemotherapeutic agent that is administered to the individual in combination with the peptide.

5 Claims, 18 Drawing Sheets
(16 of 18 Drawing Sheet(s) Filed in Color)
Specification includes a Sequence Listing.

(56) References Cited

OTHER PUBLICATIONS

Kulkarni, Abhijeet D. et al, "Polyelectrolyte complexes: mechanisms, critical experimental aspects, and applications", Artificial Cells, Nanomedicine, and Biotechnology, Jan. 12, 2016, pp. 1615-1625, vol. 44, issue 7.
Hancock, Robert E.W. et al, "The immunology of host defence peptides: beyond antimicrobial activity", Nature Reviews Immunology, Apr. 18, 2016, pp. 321-334, vol. 16.
Arranz-Trullen, Javier et al, "Host Antimicrobial Peptides: The Promise of New Treatment Strategies against Tuberculosis", Frontiers in Immunology, Nov. 7, 2017, p. 1499, vol. 8.
Marciel, Amanda B. et al, "Bulk and nanoscale polypeptide based polyelectrolyte complexes", Advances in Colloid and Interface Science, Jan. 2017, pp. 187-198, vol. 239.

ANTICANCER PEPTIDES THAT SYNERGISTICALLY ENHANCE CHEMOTHERAPEUTIC POTENCY

CROSS-REFERENCE TO RELATED APPLICATIONS

This application claims priority to U.S. provisional patent application No. 62/979,897, filed Feb. 21, 2020, and is a continuation-in-part of U.S. application Ser. No. 16/619,490, filed Dec. 5, 2019, which is a U.S. national phase application of International patent application no. PCT/US2018/035942, filed Jun. 5, 2018, which claims priority to U.S. provisional patent application 62/515,019, filed Jun. 5, 2017, the entire disclosures of each of which are incorporated herein by reference.

FIELD

The present disclosure relates generally to anti-cancer approaches are more specifically to the use of antimicrobial peptides (AMPs) to treat cancer and synergize with chemotherapeutic agents.

BACKGROUND

Chemotherapeutic resistance is a frequent cause of treatment failure in oncology, often preceding disease relapse and patient death. It is now common practice to select combinatorial cocktails of drugs with different mechanisms of action to prevent the emergence of resistant cell subpopulations. These regimens almost exclusively employ small molecule inhibitors that act on intracellular biochemical pathways, while compounds that target and disrupt the membranes of cancer cells are comparatively underexplored. Yet, there is accelerating clinical interest in adding tumor lytic agents to combinatorial therapies due to their ability to kill cancer cells through rapid, physical mechanisms that are not shared by conventional drugs.

ACPs are one such class of potential therapeutics that exert their action by preferentially intercalating into and disrupting the plasma and mitochondrial membranes of cancer cells. These membrane-destabilizing, or membranolytic, effects can promote the intracellular diffusion and passive transport of otherwise poorly permeable small molecule drugs and biologics. More importantly, the rapid and non-stereospecific mechanisms of ACPs have led to the conclusion that evolutionary resistance towards these agents is probabilistically low. Taken together, these attributes suggest that ACPs could have significant potential to advance combinatorial strategies in precision medicine if properly exploited. However, ACP discovery campaigns are constrained by the need for large empirical screens of complex natural product mixtures. These methods are costly, laborious and hindered by extensive med-chem optimization of lead candidates. There is thus ongoing and unmet need for improved approaches to cancer treatment. The disclosure is pertinent to this need.

SUMMARY

The present disclosure demonstrates use of a pathogen-specific AMP originally designed to treat multi-drug resistant (MDR) bacterial *Mycobacterium tuberculosis*. An exemplary peptide is referred to as mycomembrane-associated disruption 1 (MAD1). The disclosure demonstrates that the MAD1 peptide selectively kills cancer cells. Further, it is expected that the AMP will function in a co-treatment against cancer, where it will synergistically enhance the potency of approved chemotherapies, while exhibiting minimal cytotoxicity toward healthy cells and erythrocytes.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
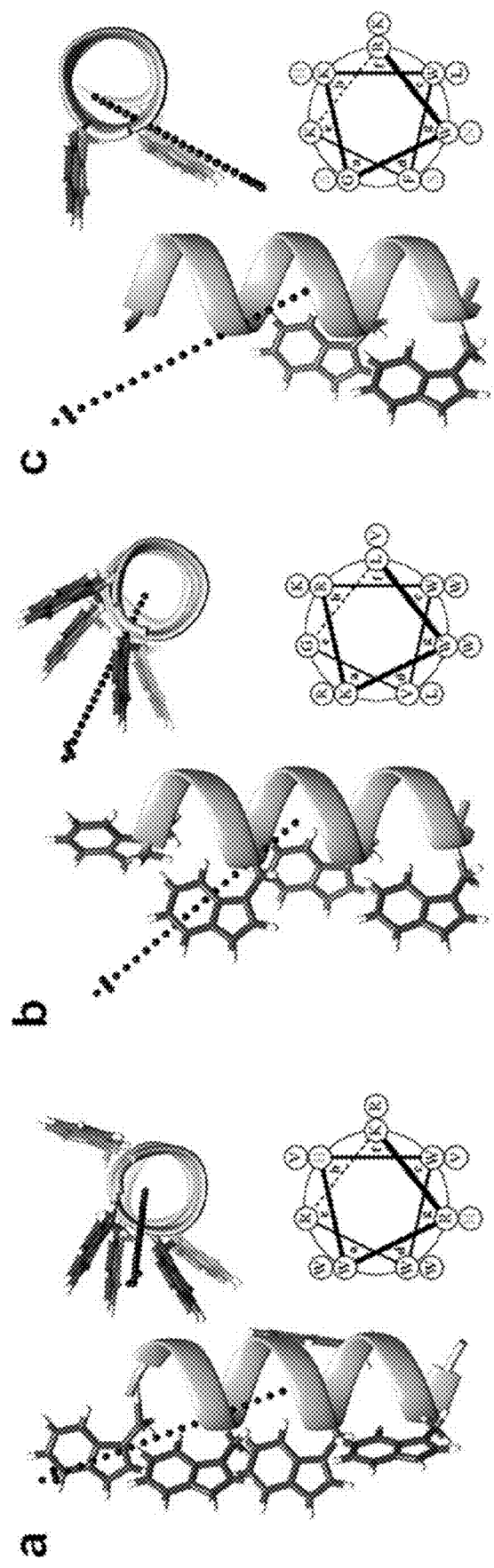
FIG. 1. Rational design of de novo anticancer peptides. Minimized model of (a) MAD1, (b) DAP1, (c) DAP2 peptide helices. For all panels, Left: helical profile; Top right: axial view (red=tryptophan residues). Vector of the hydrophobic moment shown as dotted black arrow. Bottom right: helical wheel (black=hydrophobic, blue=basic, orange=polar residues).

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

Peptides of this disclosure relate to the description of peptides in PCT/US2018/035942, filed Jun. 8, 2018, published as WO2018226614A1, from which the entire description of peptides and their amino acid sequences are incorporated herein by reference.

The disclosure includes all amino acid sequences described herein, and variants thereof. In an embodiment, the disclosure provides a peptide that exhibits anticancer activity. In one embodiment, the peptide comprises an amido group (—$NH_2$) at the C-terminus. In embodiments, a peptide of this disclosure comprises or consists of the amino acid sequence KRWHWWRRHWVVW (SEQ ID NO:1). In an embodiment, the peptide comprises an amido group at the C-terminus and thus comprises KRWHWWRRHWVVW-NH2 (SEQ ID NO:1) (MAD1).

Comparative data presented in this disclosure demonstrates that the MAD1 peptide has a superior cytotoxicity profile when analyzed using cancerous and non-cancerous cell lines, relative to comparable peptides described herein using the terms DAP1, DAP2, AMP1 and AMP2. In non-limiting embodiments, a peptide of this disclosure, such as the MAD1 peptide, exhibits at least one of the following properties: the ability to assemble on the surface of lung cancer cells (A549) and to introduce pores into the lung cancer cells; cytotoxicity against non-drug resistant cancer cells, such as ovarian cancer cells (OVCAR-3); cytotoxicity against drug resistant cancer cells, such as Adriamycin-resistant ovarian carcinoma cells (NCI/ADR-RES), as well as cytotoxicity against mammary gland adenocarcinoma cells (MDA-MB-231), and urinary bladder carcinoma cells (T24), while exhibiting no significant adverse effects against non-cancer cells (NL-20 lung endothelial cells and human umbilical vein endothelial cell (HUVECs). Thus, among its potency against representative non-drug resistant and drug resistant cancer types, the MAD1 peptide is demonstrated to exhibit an unusual specificity for human ovarian carcinomas, and synergistically enhances the activity of certain therapies that are directed to drug-refractory and -resistant tumors, as further described herein. In an embodiment, the synergistic action is shown when MAD1 is combined with the conventional chemotherapeutic agent Doxorubicin against A549 and NCI/ADR-RES cancer cells. Thus, the disclosure demonstrates a greater than additive effect against cancer cells when a peptide of this disclosure is combined with a chemotherapeutic agent. A peptide of this disclosure may also be considered to sensitize cancer cells to a chemotherapeutic agent. In embodiments, use of a peptide of this disclosure may thus overcome resistance to one or more chemotherapeutic agents. In embodiments, a described peptide is administered in combination, which may be a concurrent or sequential administration, with a chemotherapeutic agent. It is expected that administration of the peptide can have a synergistic effect with any chemotherapeutic agent, representative examples of which are described in the examples and figures. In embodiments, the chemotherapeutic agent is one or a combination of Doxorubicin (Adriamycin), Cisplatin, Cyclophosphamide, Cisplatin, Carboplatin, Pegylated Liposomal Doxorubicin, Methotrexate, Paclitaxel, Fluorouracil, Carboplatin, Paclitaxel, Docetaxel, Liposomal Doxorubicin, Gemcitabine, Cyclophosphamide Irinotecan, or Flutamide. In embodiments, a described peptide is administered in combination with one or more checkpoint inhibitors. In embodiments, the checkpoint inhibitor comprises an anti-programmed cell death protein 1 (anti-PD-1) checkpoint inhibitor, or an anti-Cytotoxic T-lymphocyte-associated protein 4 (anti-CTLA-4) checkpoint inhibitor. There are numerous such checkpoint inhibitors known in the art. For example, anti-PD-1 agents include Pembrolizumab and Nivolumab. An anti-PD-L1 example is Avelumab. An anti-CTLA-4 example is Ipilimumab. The described approaches may also be combined with other immunotherapies, such as CAR T cell therapies, and the like.

In embodiments, a peptide of this disclosure may have one or more modified amino acids that are, for example, conjugated to another moiety. In embodiments, a polypeptide of this disclosure is conjugated to at least one azido group such that it can be readily conjugated to other moieties, such as using click chemistry. In embodiments, a polypeptide of this disclosure is cyclized, or stapled. In embodiments, the peptides comprise changes in the amino acid sequences described herein. In embodiments, the change comprises a change of 1, 2, 3, 4, or 5 amino acids. In embodiments, an amino acid can be deleted, or one or more amino acids may be added. In embodiments, peptides of this disclosure may be in the form of monomers, dimers, multimers, and combinations thereof. In embodiments, any one or combination of peptides described herein can be associated with a cell membrane, such as a cell membrane of a cancer cell. In embodiments, peptides of this disclosure may be present in, for example, a recombinant fusion protein. In embodiments, the fusion protein comprises an anti-cancer agent, a non-limiting embodiment of which comprises a toxin.

In embodiments, pharmaceutical compositions comprising one or more peptides described herein are provided. In embodiments of the present disclosure, the peptides can be provided in pharmaceutical compositions by combining them with any suitable pharmaceutically acceptable carriers, excipients and/or stabilizers. Examples of pharmaceutically acceptable carriers, excipients and stabilizer can be found in Remington: *The Science and Practice of Pharmacy* (2005) 21st Edition, Philadelphia, Pa. Lippincott Williams & Wilkins, the disclosure of which is incorporated herein by reference. For example, suitable carriers include excipients, or stabilizers which are nontoxic to recipients at the dosages and concentrations employed.

In embodiments, one or more peptides of this disclosure is/are administered in a therapeutically effective amount. For any such agent, the therapeutically effective amount, e.g., a dose, can be estimated initially either in cell culture assays or in animal models. An animal model can also be used to determine a suitable concentration range, and route of administration. Such information can then be used to determine useful doses and routes for administration in humans. A precise dosage can be selected by the individual physician in view of the patient to be treated. Dosage and administration can be adjusted to provide sufficient levels of the active moiety or to maintain the desired effect. Additional factors which may be taken into account include the stage and type of cancer, the age, weight and gender of the patient, desired duration of treatment, method of administration, time and frequency of administration, drug combination(s), reaction sensitivities, and tolerance/response to therapy. A therapeutically effective amount is an amount that reduces one or more signs or symptoms of a disease, and/or reduces the severity of the disease. A therapeutically effective amount may also inhibit or prevent the onset of a disease, or a disease relapse. In embodiments, a therapeutically effective amount is an amount that reduces or eliminates cancer cells from an individual. In embodiments, a therapeutically effective dose inhibits growth of cancer cells, such as cancer cells in a tumor. In embodiments, a therapeutically effective dose inhibits formation of a primary tumor, and/or inhibits metastasis from a tumor.

The type of cancer treated according to this disclosure is not particularly limited. In embodiments, the cancer cells are of any cancer type, including solid and liquid tumors. In embodiments, cancer cells modified according to this disclosure include but are not necessarily limited to breast cancer, prostate cancer, pancreatic cancer, lung cancer, liver cancer, ovarian cancer, cervical cancer, colon cancer, esophageal cancer, stomach cancer, bladder cancer, brain cancer, testicular cancer, head and neck cancer, melanoma, skin cancer, any sarcoma, including but not limited to fibrosarcoma, angiosarcoma, adenocarcinoma, and rhabdomyosarcoma, and any blood cancer, including all types of leukemia, lymphoma, or myeloma. In embodiments, the disclosure comprises selecting an individual who has been diagnosed with cancer, and administering a described peptide to the individual. The method may further comprise testing the individual to determine the efficacy of the described therapy, e.g., monitoring the status of the cancer in the individual over a period of time subsequent to, or during a peptide dosing regimen.

In embodiments, a composition comprising one or more peptides described herein is administered to an individual who previously had cancer, or is at risk for developing cancer, and thus prophylactic approaches are included by this disclosure. The cancer can be any of the aforementioned types. The individual may also have a bacterial infection that is coincident with the cancer. But the disclosure includes the proviso that a described peptide may be administered to an individual who does not have, and/or who has not been diagnosed with, a bacterial infection.

Peptides and compositions comprising peptides of this disclosure may be administered to an individual in need thereof using any suitable route. In embodiments, the individual is human, but in certain approaches, the described peptide and methods may be adapted for use in non-human mammals, and thus the described approaches are considered suitable for veterinary approaches, such as for canines and felines.

In embodiments, the peptides may be administered by an intra-tumor injection. In embodiments, nanoparticles or other suitable drug delivery reagents such as liposomes may be used such that the peptide(s) is contained by the reagent. In embodiments, the peptides may be provided in one or more anionic polymer matrix and cationic polymer drug delivery carriers. In embodiments, the drug delivery reagent may be provided in association with a binding partner that binds specifically to a cancer cell marker. In embodiments, the binding partner comprises a cancer cell surface receptor ligand. In embodiments, the binding partner comprises an antibody, or antigen binding fragment thereof. The type of antibody or other binding partner is not particularly limited, and may comprise, for example, an ScFv, a single chain antibody, single domain antibodies (sdAbs, VHHs or nanobodies), affibodies or Darpins.

In embodiments, when delivered such that the peptide and drug delivery reagent are specifically targeted to cancer cells, the administration may comprise any suitable route, including oral, parenteral, subcutaneous, intraperitoneal, intrapulmonary, and intranasal, and intracranial. Parenteral infusions include intramuscular, intravenous, intraarterial, intraperitoneal, and subcutaneous administration.

The following examples illustrate embodiments of this disclosure and are not intended to be limiting.

EXAMPLE 1

This Example provides a description of materials and methods used to produce the results and figures of this disclosure.

Materials 1,2-ethanedithiol and diethyl ether were purchased from Acros Organics. 1,3-bis[tris(hydroxymethyl)methylamino] propane (BTP), piperidine, dimethyl sulfoxide spectrophotometer grade (DMSO), and thioanisole were purchased from Alfa Aesar. Vascular Cell Basal Medium, Rh VEGF, rg EGF, rg FGF basic, rg IGF-1, L-glutamine, heparin sulfate, hydrocortisone hemisuccinate, FBS, and ascorbic acid were purchased from ATCC. 1-palmitoyl-2-oleoyl-sn-glycero-3-phosphocholine (POPC), 1-palmitoyl-2-oleoyl-sn-glycero-3-phospho-L-serine (POPS), and 1,2-dioleoyl-sn-glycero-3-phosphoethanolamine (DOPE) were purchased from Avanti Polar Lipids. FITC Annexin V Apoptosis Detection Kit with PI was purchased from BioLegend. 0.2 μm nitrocellulose membrane were purchased from Bio-Rad. Cleaved Caspase-3 Rabbit Ab and β-Actin (8H10D10) Mouse mAb were purchased from Cell Signaling Technology. Fmoc-protected amino acids, oxyma, and Rink Amide ProTide Resin were purchased from CEM. Paraformaldehyde was purchased from Chem Cruz. 3-(4,5-Dimethyl-2-thiazolyl)-2,5-diphenyl-2H-tetrazolium bromide (MTT), Fmoc-protected amino acids, N,N⁰-diisopropylcarbodiimide (DIC), O-(7-Azabenzotriazol-1-yl)-N,N,N',N'-tetramethyluronium hexafluorophosphate (HATU), N,N-dimethylformamide (DMF), and Paclitaxel were purchased from Chem-Impex International, Inc. RPMI-1640, M199, trypsin and EDTA solution, Antibiotic-Antimycotic Solution, ultra-low attachment (ULA) plates, and 1×phosphate buffered saline (PBS) were purchased from Corning. Fetal bovine serum was purchased from HyClone. Hoechst 33342 trihydrochloride trihydrate dye was purchased from Invitrogen. Goat antimouse IgG (LC Specific) and Peroxidase AffiniPure Goat Anti-Rabbit IgG (H+L) were purchased from Jackson ImmunoResearch. Glycerol, tween 80, oadc supplement, MEM non-essential amino acid solution, D-(+)-Glucose, Insulin (Recombinant human), Transferrin Apo-(human plasma), hydrocortisone, OmniPur® Tween® 20 (Polyoxyethylene (20) Monolaurate), and sodium bicarbonate were purchased from Millipore-Sigma. N,N-Diisopropylethlamine (DIEA) and Doxorubicin HCl were purchased from Oakwood. 5% Blotto Immunoanalytical Grade (Non-Fat Dry Milk) was purchased from Rockland Immunochemicals. Cisplatin was purchased from Selleck Chemical S1166. MCDB-105 and FCCP (2-[2-[4-(trifluoromethoxy)phenyl]hydrazinylidene]-propanedinitrile) were purchased from Sigma-Aldrich. Cisplatin was purchased from Tocris Bioscience. Lysogeny broth, Mueller Hinton broth, 7H9 media, Nunc Lab-Tek Chambered Coverglass, sodium chloride (NaCl), hydrochloric acid (HCl), acetonitrile, trifluoroacetic acid (TFA), dichloromethane, dimethyl sulfoxide cell culture grade (DMSO), NHS-Fluorescein, 3500 MWCO Slide-A-Lyzer Dialysis Cassettes, Pierce ECL Western Blotting Substrate, SuperSignal West Dura Extended Duration Substrate, and formic acid LC/MS grade were purchased from ThermoFisher Scientific. Anisole was purchased from Tokyo Chemical Industry. F12 media, L-glutamine, sodium fluoride, sodium hydroxide, sodium phosphate monobasic, and sodium phosphate dibasic were purchased from VWR.

Analytical LCMS solvents were composed as follows: solvent A is 0.1% formic acid in water and solvent B is 9:1 acetonitrile and water with 0.1% formic acid. Preparative HPLC solvents consisted of solvent A (0.1% TFA in water) and solvent B (9:1 acetonitrile and water with 0.1% TFA).

Peptide Synthesis

Peptide synthesis reactions were performed as previously described, using Fmoc-based solid phase peptide synthesis with Oxyma/N,N'-Diisopropylcarbodiimide (DIC) activation on Rink Amide ProTide resin using a Liberty Blue Automated Microwave Peptide Synthesizer (CEM, Matthews, N.C.). To prepare fluorescently labeled peptides, MAD1 was further reacted on resin with 2 equivalents of NHS-Fluorescein (5/6-carboxyfluorescein succinimidyl ester) and 4 equivalents of diisopropylethalamine in DMF, and allowed to shake at room temperature for 4 hours. Reaction progress was checked via Kaiser test to detect free amines.

Cleavage from the resin and de-protection was completed by stirring the crude with a trifluoroacetic acid:thioanisole:1,2-ethanedithiol:anisole (90:5:3:2) solution under a constant stream of argon. MAD1 was stirred at 30° C. for 3 hours and DAP1/DAP2 were stirred for 2.5 hours at room temperature. To precipitate the peptide from the deprotection cocktail, cold diethyl ether was added, followed by centrifugation at 5,000 rpm for 8 min. After decanting the diethyl ether, the sample was lyophilized overnight to remove remaining trace amounts of organic solvent. Crude peptides were purified on a Phenomenex Semi-Prep Luna C18(2) column (Torrance, Calif.) by reverse-phase HPLC (Shimadzu, Columbia, Md.). MAD1 was purified using a linear gradient of 0-25% solvent B over 25 min., followed by a linear gradient of 25-45% solvent B over 40 min. Purification of FITC-labeled MAD1 analogue was performed using a linear gradient of 0-12% solvent B over 6 min., followed by 12-32% solvent B over 20 min., and finally 32-38% solvent B over 12 min. For DAP1 peptide purification, a linear gradient of 0-42% solvent B over 38 min. was used. For DAP2 peptide purification, a linear gradient of 0-10% solvent B was used over 10 min. followed by a linear gradient of 10-25% solvent B over 30 min. After lyopholization to collect pure peptide, all compounds were characterized by LC-MS ESI (+) to confirm purity >95% via MS peak integration (FIGS. 7-10).

Cell Cytotoxicity and Combinatorial Assays

All cells were cultured using standard culture conditions at 37° C., 5% $CO_2$, and 95% humidity. A549 (CCL-185), OVCAR-3 (HTB-161), T24 (HTB-4), and NCI/ADR-RES were cultured in RPMI-1640 supplemented with 10% v/v fetal bovine serum (FBS), 2 mM L-glutamine (L-Gln), 10,000 units penicillin/mL, 10 mg/mL streptomycin, and 25 µg/mL amphotericin B. HUVEC (PCS-100-010) cells were cultured in Vascular Cell Basal Media (PCS-100-030) supplemented with an Endothelial Cell Growth Kit-VEGF (PCS-100-041) and 10 µg/mL gentamycin in culture flasks coated with 0.1% gelatin by incubating at 37° C. for 15 min. NL20 (CRL-2503) cells were cultured in Ham's F12 supplemented with 1.5 g/L sodium bicarbonate, 2.7 g/L glucose, 2.0 mM L-glutamine, 0.1 mM nonessential amino acids, 0.005 mg/ml insulin, 10 ng/ml epidermal growth factor, 0.001 mg/ml transferrin, 500 ng/ml hydrocortisone and 4% fetal bovine serum, as advised by American Type Culture Collection (ATCC).

For cytotoxicity experiments, cells were first seeded in 96 well plates at $5 \times 10^3$ cells/well for A549, OVCAR-3, T24, and NCI/ADR-RES cells, and $10 \times 10^3$ cells/well for HUVEC and NL20 cells. After 24 hours of incubation to allow the cells to adhere, the media was aspirated and 100 µL of treatments prepared in media with 5% FBS were added to each well; blank media and 20% DMSO served as negative and positive controls, respectively. Treatments were allowed to incubate for 48 hours, followed by cell viability determination by MTT assay. In brief, wells were aspirated and replaced with 100 µL of 0.5 mg/mL thiazolyl blue tetrazolium bromide dissolved in media. The plates were allowed to incubate for 2-3 hours and were then lysed with 100 µL of DMSO to dissolve the converted formazan product. Absorbance of the wells was measured via a microplate reader (Biotek, Winooski, Vt.) at 540 nm; percent viability was calculated by subtracting the positive control and normalizing to the negative control. To verify results from MTT assays, cell counting was used to as a secondary measure of cell death. Following MAD1 treatment, as described above, cells were fixed with 4% paraformaldehyde in PBS before staining the nuclei with Hoechst 33342. Five images were taken at each concentration using an Olympus IX73 microscope (Tokyo, Japan) will the well centered in the view field. Cell counting was performed by Matlab code modified from publicly available source at //www.mathworks.com/help/images/ref/regionprops.html. Viability was calculated by comparing to an untreated control. Results were plotted in GraphPad Prism software with standard deviation reported.

For individual peptide cytotoxicity experiments, MAD1, DAP1, DAP2, AMP1, and AMP2 treatments were serially diluted to 100-0.001 µM concentrations. For individual chemotherapeutic experiments, doxorubicin, paclitaxel, and cisplatin were diluted 1:10 six times from 100 µM, 100 nM, and 100 µM, respectively. All treatments were prepared first as a stock solution in water and subsequently diluted into standard media with 5% FBS; paclitaxel and cisplatin stock solutions were first prepared in DMSO before diluting into media with a final DMSO concentration <0.1%. All experiments were performed with n>6.

For combinatorial cytotoxicity experiments, 96 well plates were set up in a checkerboard fashion such that peptide decreased in 1:10 concentration dilutions in one direction and chemotherapeutic decreased in 1:10 concentration dilutions in the orthogonal direction. 2×treatments were combined prior to cell administration for a final 1×concentration to prevent individual treatment effects. Experiments were performed in triplicate and heat maps were generated with MATLAB using logarithmic interpolation to obtain drug $IC_{50}$ values at 20 µM MAD1.

Bacterial Cultures and Minimum Inhibitory Assays

For bacterial assays, bacteria were cultured according to the following established methods. *Bacillus subtilis* (168) was cultured in lysogeny broth (LB). *Escherichia coli* (dh5-α), *Pseudomonas aeruginosa* (PAO-1), methicillin-resistant *Staphylococcus aureus* (MRSA; nrS72), and methicillin-sensitive *Staphylococcus aureus* (MSSA; usa300) were cultured in cation adjusted Mueller-Hinton broth (CAMHB). *Mycobacterium tuberculosis* (h37ra) was cultured in Middlebrook 7H9 supplemented with 0.05% (v/v) polysorbate 80, 0.5% (v/v) glycerol and 10% (v/v) oleic acid-albumin-dextrose-catalase (OADC). Each culture was grown in a shaking incubator at 37° C. at 200 rpm, according to guidelines provided by the Clinical and Laboratory Standards Institute (CLSI).

For MIC studies, peptide was first prepared in water at 320 µL (4×) and diluted 1:2 in appropriate treatment broth. Bacteria were prepared in appropriate media and diluted to an $OD_{600}$=0.002. Next, 50 µL of treatment broth was added to each well in rows 2-8 of a 96 well plate, with the first three columns containing untreated broth as a negative control. In row 1, 100 µL of the 2×peptide in broth was added. Using a multi-channel pipette, 50 µL of the 2×peptide solution was diluted 1:2 in the subsequent row and repeated for all rows. 50 µL of bacteria was added to each well, incubated for 24 hours, and read using visual evaluation. The MIC, or minimum inhibitory concentration, was determined by the lowest concentration with a significant reduction in bacteria pellet presence compared to the negative control.

Particle Formulation

Liposomes were prepared by extrusion techniques according to previous methods. Briefly, all liposomes were prepared in 2×concentration (5 mM). Healthy and cancer liposomal mimicking membranes were prepared with 72:23:5 and 45:24:30 phosphatidylcholine (POPC):phosphatidylethanolamine (DOPE):phosphatidylserine (POPS) lipids, respectively. The lipids dissolved in chloroform were mixed in proper molar proportions before being evaporated under a stream of argon. The lipid film was then dried completely by lyophilization overnight. Then, the lipids were rehydrated in 2×concentrated liposomal buffer (300 mM BTP, 100 mM NaF, and pH 7.4) before 8 freeze/thaw cycles in liquid nitrogen and water bath 37° C. The membranes were then extruded using an Avanti Mini Extruder (Alabaster, Ala.) with a 0.1 µM nuclepore polycarbonate membrane >11 times. The extruded liposomes were then dialyzed in 3500 MWCO dialysis cassettes against water.

Circular Dichroism

Circular dichroism (CD) was performed using 20 mM sodium phosphate buffer (15.1 mM sodium phosphate dibasic heptahydrate, 0.49 mM sodium phosphate monobasic monohydrate, and pH 7.4) and a J-1500 Circular Dichroism Spectrometer (JASCO, Oklahoma City, Okla.). In a 1 mm path length quartz cell, 150 µL of membrane mimicking liposomes were combined with 150 µL of 200 µM peptide in buffer and exposed to a wavelength spectrum of 180 to 260 nm at 25° C. Mean residue molar ellipticity [θ], measured in ($10^{-1}$.deg.cm$^2$.dmol$^{-1}$), was normalized using the following expression:

$$\frac{\theta_{meas}}{100 \cdot 10 * l \cdot c * r}$$

where $\theta_{meas}$ is ellipticity (mdeg), $l$ is light path length (cm), c is molar concentration (mol/L), and r is number of amino acid residues.

Parallel optical density experiments were conducted measuring the absorbance at 600 nm ($OD_{600}$) to track the kinetics and specificity of membrane disruption. Measurements were taken every 30 seconds for the first 10 min., followed by measurements every minute until 15 min.

Scanning Electron Microscopy

SEM was conducted on OVCAR-3 cells after first being seeded onto uncoated glass coverslips in a 12 well plate at $3 \times 10^4$ cells/well and allowed to adhere overnight. Next, the cells were treated with 10 µM of peptide in 5% FBS media for 1 or 4 hours, and a negative control in peptide-free media. The cells were then washed with fresh serum free media and fixed with cold 5% glutaraldehyde in 0.1 mM sodium cacodylate and left overnight at 4° C. The cells were subsequently rinsed three times with 0.1 mM sodium cacodylate before being subjected to an ascending ethanol dehydration series (25,50,70,85,90,95,100%). The cells were stored in 100% ethanol before transferring to a Leica EM CPD300 Critical Point Dryer (Buffalo Grove, Ill.). Dried samples were mounted onto metal SEM stubs using double sided carbon tape, and sputter coated with Au/Pd 60:40 using a Bal-tec SCD-050 Sputter Coater (Capovani Brothers Inc., Scotia, N.Y.). Finally, samples were imaged using a Zeiss SIGMA VP-FESEM (Thornwood, N.Y.) using secondary electron imaging. Experiments were performed in duplicate.

Confocal Fluorescent Microscopy

OVCAR-3 cells were seeded at $3 \times 10^4$ cells/well in a chambered coverslip and allowed to adhere for 24 hours. Cells were treated at the peptide $IC_{50}$ as determined by preliminary experimentation in serum free media for 1 hour, 4 hours, and 10 hours. Serum free media was used as a negative control. After treatment incubation periods, cells were washed with cold PBS and fixed with 4% paraformaldehyde for 20 min. at room temperature. After washing with cold PBS, 2 µg/mL Hoechst in PBS was added and left to incubate for 20 min. Slides were imaged on an Olympus Fluoview 1000 Confocal Microscope (Olympus, Shinjuku, Tokyo, Japan) with a PlanApo 60X/1.4 oil objective lens using 405 nm and 488 nm single photon lasers for DAPI and FITC, respectively.

Western Blotting

For western blots, OVCAR-3 cells were first seeded at $2.5 \times 10^5$ cells/well in a 6 well plate and allowed to adhere overnight. Cells were then treated in 5% FBS media with $1 \times IC_{50}$ and $2 \times IC_{50}$, with untreated controls of media alone. Following 2 or 48 hours of treatment, the whole-cell protein lysates were prepared in RIPA buffer (50 mM Tris.NaOH at pH 7.4, 150 mM NaCl, 1% IGEPAL-CA630 [octylphenoxy poly(ethyleneoxy)ethanol], 0.5% sodium deoxycholate, 0.1% SDS, 2 mM EDTA, protease/phosphatase inhibitors) by first scraping the bottom of the well and subsequently briefly sonicated. The lysates were centrifuged to clear cellular debris, separated by 12% SDS-PAGE, and transferred to a 0.2 µm Nitrocellulose Membrane using the Bio-Rad Trans-Blot Turbo transfer machine (Bio-Rad, Hercules, Calif., USA) according to the manufacturer's protocols. The blot was incubated in 5% Immunoanalytical Grade Non-fat Dry Milk for 1 hour, followed by incubation with antibodies against cleaved caspase-3 (1:1000) or actin (1:1000) at 4° C. for 16 hours. The blots were then incubated with 1:2000 dilution in 1×BSA of anti-mouse or anti-rabbit antibodies for 1 hour before washing with TBST three times for 15 min. and developing using Pierce ECL system according to the manufacturer's protocol.

Flow Cytometry

OVCAR-3 cells were first seeded at $2 \times 10^5$ cells/well in 12 well plates. The cells were then allowed to adhere overnight. Treatments were conducted at $1 \times IC_{50}$ of MAD1 at 2 and 24 hours in culture media adjusted to 5% serum. Wells were left in 5% serum media for negative and compensation controls. Cells were then trypsinized, washed in cold PBS, and centrifuged at 3,000 rpm at 15° C. for 5 min. After the supernatant was aspirated, the cells were resuspended in 100 µL of Annexin V Binding Buffer. In the dark, 5 µL of FITC Annexin V and 10 µL of Propidium Iodine solution were added to the cells, with compensation controls of a negative control with no staining, a FITC Annexin V only control, and a PI only control. The cells were then vortexed gently to combine and allowed to incubate for 15 min. at room temperature. 400 µL of Annexin V Binding Buffer was then added to each tube and stored on ice prior to analyzing by flow cytometry.

Flow cytometry was conducted on a LSRFortessa Flow Cytometer (BD Biosciences, Franklin Lakes, N.J.) using 488 nm and 532 nm lasers for FITC and PE-Texas Red signals to detect Annexin V and PI, respectively. Compensation was completed for 10,000 cells, and experiments were conducted over 20,000 cells.

Tetramethylrhodamine, Ethyl Ester (TMRE) Flow Cytometry

OVCAR-3 cells were treated with the indicated concentrations of MAD1 peptide for 48 hours or the positive control FCCP (2-[2-[4-(trifluoromethoxy)phenyl]hydrazinylidene]-propanedinitrile) for 5 min. (5 µM). Cells were incubated for 30 min. with 200 nM TMRE, washed twice with PBS, and analyzed for fluorescence by flow cytometry on a BD FACSCanto 10 (BD Biosciences, Franklin Lakes, N.J.).

Spheroid Culturing

OVCAR-3 cells were cultured using RPMI 1640 supplemented with 5% FBS and 1% penicillin-streptomycin. EOC patient-derived cells were cultured in 1:1 MCDB-105: M199 supplemented with 10% FBS and 1% penicillin-streptomycin. EOC patient-derived cells were provided by Dr. Katherine M. Aird under an Institutional Review Board-approved protocol. EOC patient-derived cells were collected from patient ascites fluid after paracentesis procedures. Cells were routinely tested for mycoplasma as previously described. OVCAR-3 and patient-derived cells (EOC15, EOC17, and EOC19) were seeded at $1 \times 10^5$ cells/well in ultra-low attachment (ULA) plates. 24 hours after seeding, spheroids were treated alone or in combination with 2 µM cisplatin and/or 4 µM MAD1 peptide for 48 hours. After 48 hours, 10×images were taken of the spheroids (Nikon Elements Ts2, Nis Elements F 4.51.00). Spheroid length and width was calculated using ImageJ. Spheroid volume was calculated using the following equation $$\frac{(W^2)*L}{2}.$$

Experiments were performed in triplicate at least two independent times.

Statistical Methods

Cell viability experiments were completed n>6 in two independent experiments and analyzed using GraphPad Prism 8 to fit curves and calculate $IC_{50}$ values using inhibitor vs. normalized response non-linear regression model. $IC_{50}$ values are reported as mean values±standard deviation. For bacterial MIC experiments, values are reported as the average of 3 replicates. Pore size frequency distribution was completed by ImageJ FIJI on 4 independent cells and n=30 pores from SEM images. UV-Vis $OD_{600}$ and CD spectra are means of 5 and 3 replicates, respectively and reported as mean±standard deviation. Individual UV-Vis and CD spectra, as well as fluorescent confocal and TEM micrographs, shown are representative plots from three individual experiments. CD data is with a variance in ellipticity of 0.2 millidegrees at each wavelength. Relative fluorescence data calculated from fluorescent confocal images represents the average of 10 independent measurements±standard deviation. For spheroid volume analysis, a Kruskal-Wallis test and Dunn's multiple comparisons test was performed using GraphPad Prism 8.

EXAMPLE 2

Figure 2:
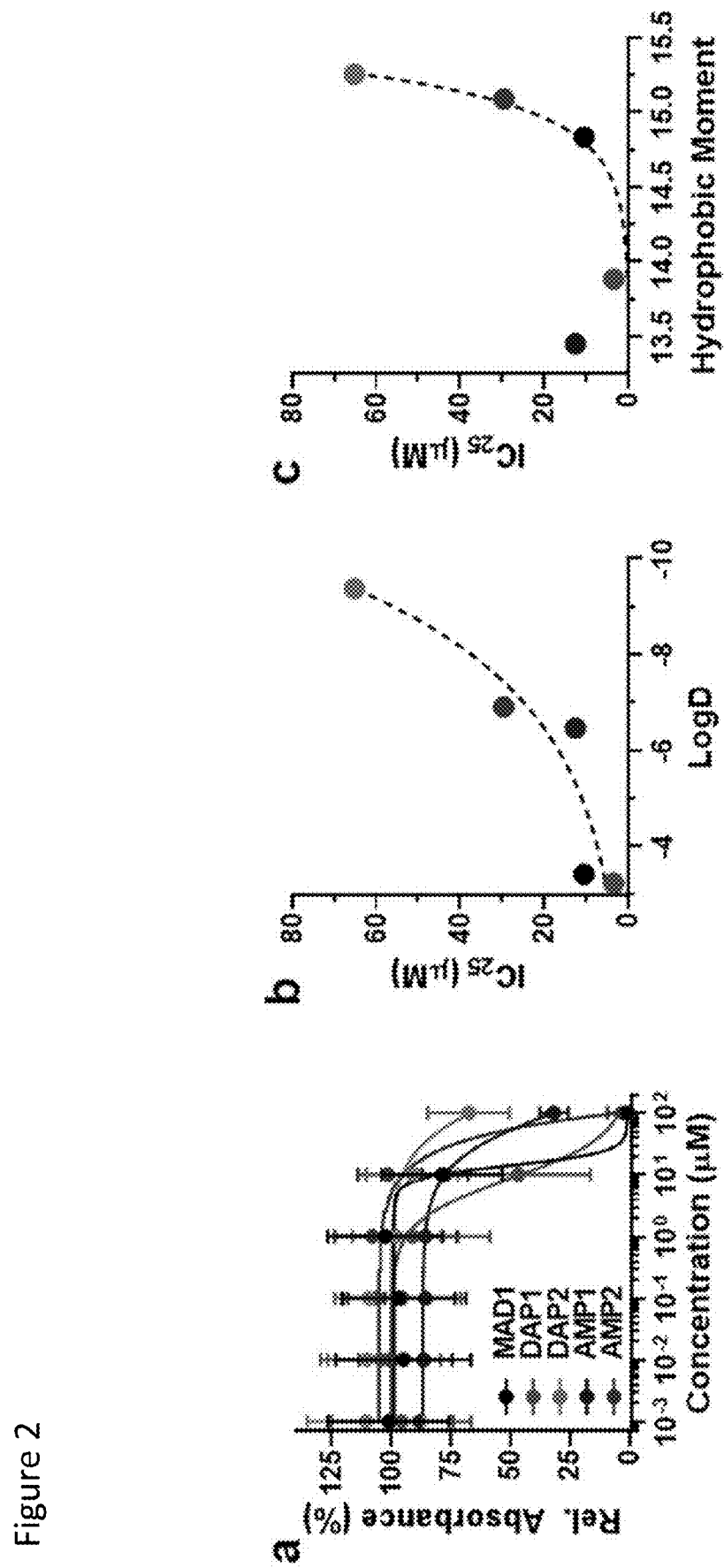
FIG. 2. ACP cytotoxicity and structure-activity relationships. (a) Cytotoxicity curves for MAD1, DAP1, DAP2, AMP1, and AMP2 peptides against OVCAR-3 ovarian carcinoma cells, shown as percent relative MTT absorbance. Curves for all four cancer cell lines tested are shown in FIG. 12. Relative change in OVCAR-3 $IC_{25}$ value as a function of (b) sequence hydrophobicity (logD) and (c) helix facial amphiphilicity (hydrophobic moment). Exponential fit (dashed line, GraphPad Prism) included to guide the eye.
Figure 11:
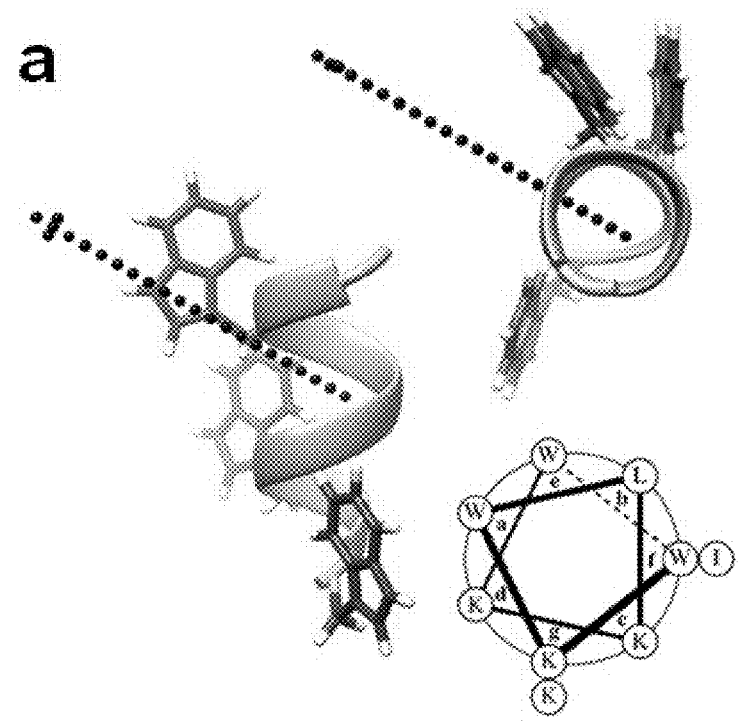
FIG. 11. Minimized model of (a) AMP1 and (b) AMP2 peptide helices. Left: helical profile; Top right: axial view (red=tryptophan residues). Vector of the hydrophobic moment shown as dotted black arrow. Bottom right: helical wheel (black=hydrophobic, blue=basic residues).
Figure 11:
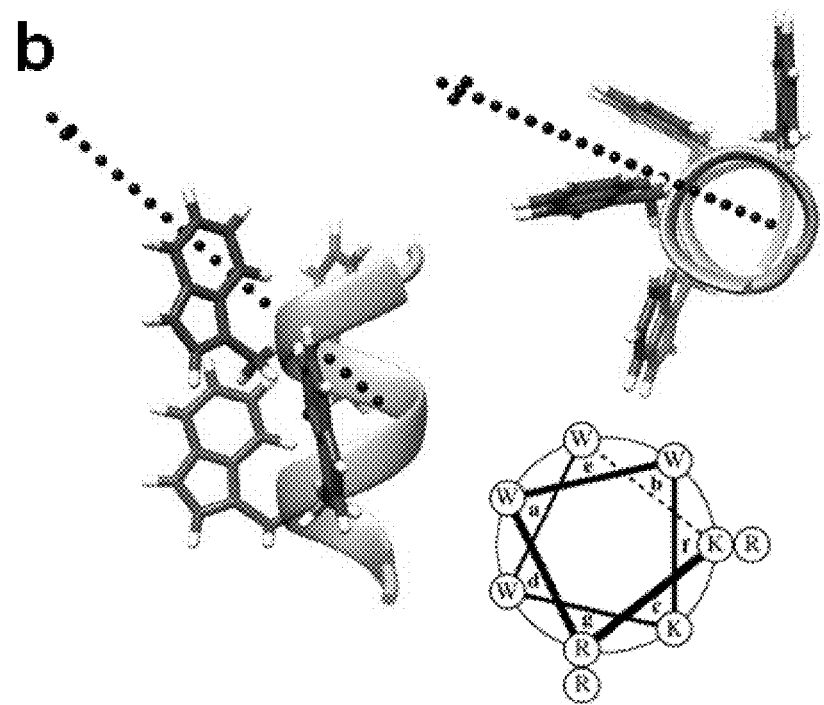
Figure 12:
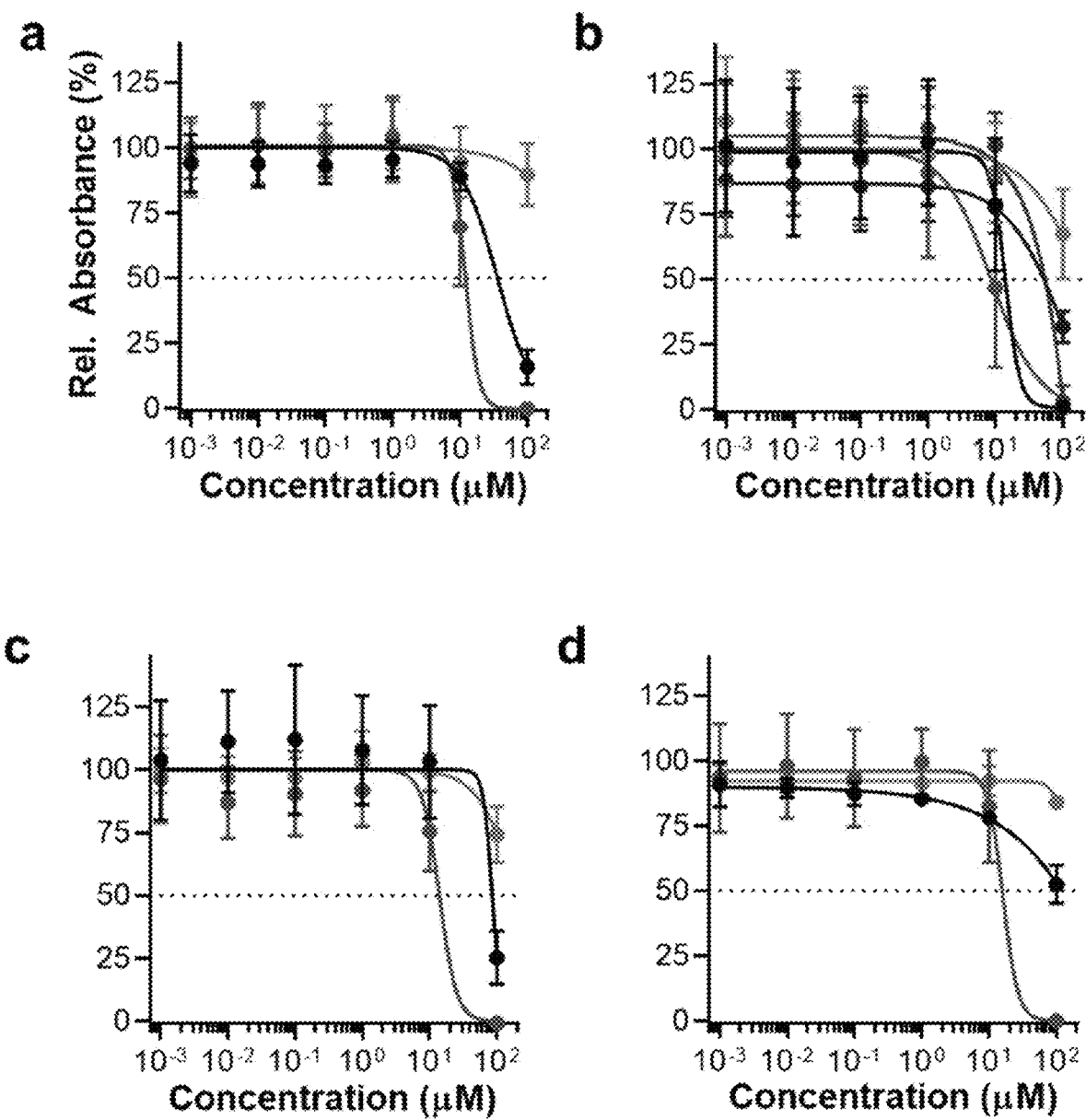
FIG. 12. Cytotoxicity curves for MAD1 (black), DAP1 (red) and DAP2 (green), peptides against (a) A549 (lung carcinoma), (b) OVCAR-3 (ovarian carcinoma), (c) NCI/ADR-RES (drug-resistant ovarian carcinoma) and (d) T24 (urinary bladder transitional cell carcinoma) cells. AMP1 (blue) and AMP2 (purple) were included in OVCAR-3 viability experiments (b) to aid SAR interpretation of ACP potency, as presented in FIG. 2 of the main text. Results shown as percent relative MTT absorbance, and dashed line included to mark $IC_{50}$.
Figure 13:
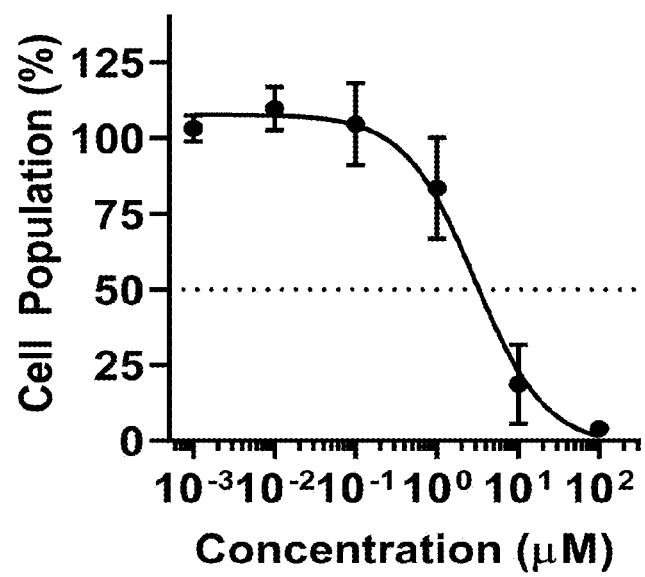
FIG. 13. Cytotoxicity of MAD1 against OVCAR-3 cells, as determined by replicate cell nuclei counting from confocal microscopy images. Results shown as normalized cell population percentage, and dashed line included to mark $IC_{50}$.

This Example provides a description of representative peptides of the disclosure and comparative data. Key to MAD1's bactericidal action is its ability to adopt a facially amphiphilic alpha helix that is defined by a hydrophobic, tryptophan-rich surface (FIG. 1a). Intermolecular zippering of tryptophan side chains enables supramolecular assembly of MAD1 peptides to form a lytic nanostructure within the Tuberculosis pathogen cell wall. Given its antimicrobial importance, we first investigate the role of this tryptophan-rich helical surface on the potential anticancer activity of MAD1. To do this we designed two ACP analogues, DAP1 and DAP2 (de novo designed anticancer peptide), in which both sequences exhibit variations in hydrophobic amino acid packing and spatial display relative to the MAD1 template. For DAP1, the cationic and hydrophobic faces of the helix are spatially segregated with respect to each other (see helical wheel in FIG. 1b, bottom), resulting in a more uniform angular alignment of tryptophan residues in the axial direction. To accommodate this dense packing of hydrophobic groups, the number and spacing of lysine and arginine residues was altered for the DAP1 scaffold. Collectively this design leads to an increase in sequence hydrophobicity (defined by logD value) and a decrease in helical hydrophobic moment (a vector-based measure of helix amphiphilicity) of DAP1 compared to MAD1 (Table 1). Conversely, DAP2 is designed such that tryptophan residues are axially isolated to only the N-terminal half of the peptide, leading to a decrease in the overall hydrophobic surface area relative to MAD1 (FIG. 1c). This results in a significant decrease in hydrophobicity, as defined by a reduction of its logD value, and corollary increase in hydrophobic moment for DAP2 relative to MAD1. To further deconvolute the effects of logD and hydrophobic moment on ACP potency in later studies, we also included two additional tryptophan-rich antimicrobial peptides, AMP1 and AMP2. AMP1 exhibits a similar spatial distribution of tryptophan residues, and thus an analogous hydrophobic moment, as DAP1 (FIG. 11a, Table 1) but is significantly more hydrophilic (logD=−6.46). AMP2, on the other hand, is defined by facially segregated amphiphilic regimes (see helical wheel in FIG. 11b) that impart it with a comparable hydrophobic moment as DAP2, while the logD value remains consistent with AMP1. Together, these peptides allow systematic evaluation of how changes in sequence logD and hydrophobic moment influence their cytotoxic effects, with the expectation that anticancer potency will follow DAP1>MAD1>AMP1>AMP2>DAP2. To test this assertion, we measured the cytotoxicity of each sequence against a panel of human cancer cell lines, as well as non-cancerous controls (FIG. 2a, Table 2 and FIG. 12). As predicted, DAP1 was the most potent ACP of the five sequences, with $IC_{50}$ values that ranged from 8.6-15.3 µM, dependent on cell line. MAD1 displayed preferential activity towards the ovarian carcinoma cell line OVCAR-3 ($IC_{50}$=14.2 µM, FIG. 2a), moderate activity against A549 (lung carcinoma) and NCI/ADR-RES (drug resistant ovarian cancer) cells, and was inactive towards T24 (bladder cancer). Given that these results are derived from MTT experiments, which measures mitochondrial activity and thus subject to artifacts from metabolic quiescence, we performed a secondary nuclei-counting assay (FIG. 13). These results support the claim that MAD1 mediates toxicity by killing, or inhibiting the growth, of OVCAR-3 cells ($IC_{50}$=3.3 µM) and is not solely a result of changes in cellular metabolism. Finally, consistent with our expectations, AMP1 and AMP2 were less effective compared to DAP1 and MAD1 ($IC_{50}$≈50 µM, FIG. 2a) in OVCAR-3 cells, while DAP2 was inactive towards all four of the tumor cell lines tested.

Interestingly, although DAP1 was the most potent ACP of the five peptides, it showed nearly equal toxicity against the two non-cancerous cell lines tested: human umbilical vein endothelial cells (HUVEC) and human lung epithelium (NL20). Accordingly, this defines therapeutic indices, a quantitative measure of relative drug safety, for DAP1 of ≤2.3 (Table 2). MAD1 on the other hand was well tolerated by both control cell lines and, as a result, generally possessed superior therapeutic indices compared to DAP1. Notably, MAD1 displayed an index of 7 towards OVCAR-3 cells, suggesting a distinct selectivity of the peptide towards ovarian cancers; an assertion we later confirm in ex vivo studies. This specificity may be a result of variations in glycan composition between the tested cell lines. Ovarian cancer cells, for example, are defined by highly sialylated N-glycans displayed at the cell surface. Bladder cancer cells, on the other hand, are characterized by increased expression of neutral mannose glycans and β1,6-branched oligosaccharides. Given that many cationic ACPs preferentially engage cancer cells via binding to negatively charged sialic acid residues, this suggest MAD1-sensitive versus-insensitive cell lines may be distinguished by their glycan manifold.

The described cytotoxicity data indicates that AMPs can be re-designed to afford new ACPs (but not all ACPs exhibit predicted function). Given the shared mechanisms of action between these two classes of peptides, the reverse should also be true: ACPs can function as AMPs. To test this assertion, we measured the antimicrobial activity of MAD1, DAP1, and DAP2 against a polymicrobial panel (Table 3). MAD1 and DAP1 both displayed bactericidal activity, with DAP1 generally showing more potent broad-spectrum effects relative to the MAD1 peptide. Conversely, DAP2 is inactive towards all six of the bacterial lines tested.

EXAMPLE 3

ACP Structure-Activity Relationships and Ovarian Cancer Specificity

We further examined how anticancer potency of these peptides is influenced by their hydrophobicity (logD, FIG. 2b) and facial amphiphilicity (hydrophobic moment, FIG. 2c). For these analyses we utilized cytotoxicity data from the OVCAR-3 cell line and plotted the appropriate $IC_{25}$ value of each sequence. Here, $IC_{25}$ was chosen as DAP2 did not achieve an $IC_{50}$ at the concentrations tested (see green data in FIG. 2a). Results demonstrate a clear correlation between peptide toxicity and both sequence logD (FIG. 2b) and hydrophobic moment (FIG. 2c); with changes in the latter causing a particularly sharp shift in ACP potency. This suggests there may exist an amphiphilicity threshold that differentiates active from inactive sequences. In our studies, peptide helices with a hydrophobic moment <15 were sufficiently amphiphilic to cause potent oncolytic activity ($IC_{25}$<15 µM). Taken together, this suggests that the cytotoxic potential of a given ACP is largely dependent on a combination of its hydrophobicity and amphiphilicity, or lipophilicity. This further validates the claim of shared molecular mechanisms between ACPs and AMPs, as it is well established that lipophilicity is a key driver of AMP bacteriolytic activity.

Figure 3:
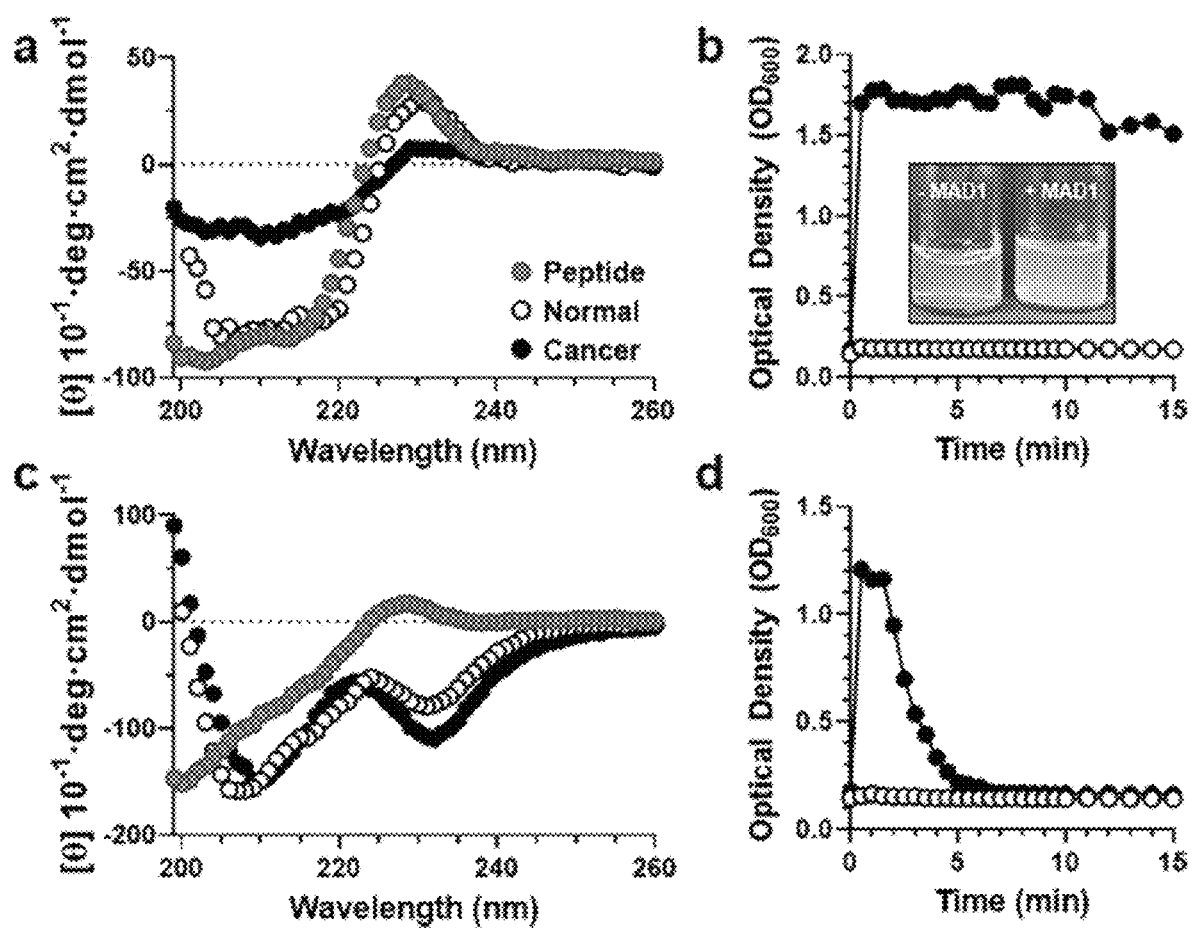
FIG. 3. Tumor membrane-templated ACP assembly. (a) Circular dichroism spectra of the MAD1 peptide in aqueous solution (✵), or in the presence of normal (○) and cancer cell (●) membrane models. (b) Relative disruption of normal (○) and cancer (●) model membranes by the MAD1 peptide, as determined from optical density measurements ($OD_{600}$). Inset: image of cancer membrane liposomal solution before (−MAD1) and after (+MAD1) treatment with the peptide. Formation of large flocculates provides visual confirmation of liposome disruption. (c) Circular dichroism spectra and (d) optical density measurements of DAP1 in the absence or presence of model membranes (✵=no membrane, ○=normal membrane, ●=cancer membrane).
Figure 14:
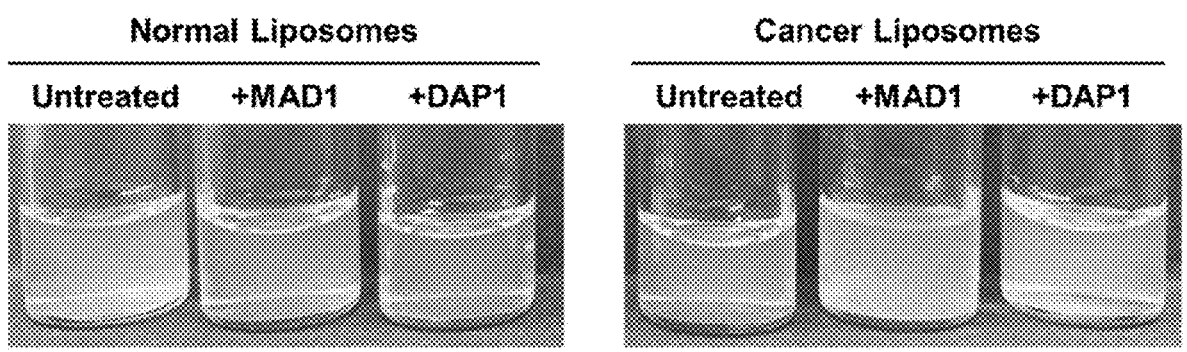
FIG. 14. Images of normal (left) and cancer (right) membrane liposomal solutions before (untreated) and after treatment with either the MAD1 or DAP1 peptide. Formation of large flocculates in cancer liposomal solutions treated with MAD1 provides visual confirmation of membrane disruption.

The described cell-based studies collectively demonstrate that MAD1 preferentially targets and disrupts cancer cell membranes over that of normal, healthy counterparts. To mechanistically investigate this, circular dichroism (CD) spectroscopy was performed to monitor changes in peptide secondary structure in the absence and presence of normal or cancerous liposomal membrane analogues. CD spectra shown in FIG. 3a demonstrate that MAD1 adopts an a-helical conformation in aqueous solutions, with characteristic minima in ellipticity at 204 nm and 216 nm. An exciton band at 228 nm is indicative of interactions between aromatic indole chromophores as a result of intermolecular tryptophan pairing between peptides. When mixed with liposomes mimicking the composition of normal mammalian cell membranes (72:23:5 POPC:DOPE:POPS), MAD1 largely maintains its a-helical structure. A slight red-shift (+2 nm) in both the Trp-Trp ellipticity maximum (230 nm) and α-helical minima (206 nm and 218 nm) suggests MAD1 benignly adsorbs to the surface of normal membranes However, when mixed with cancer membranes (45:24:30 POPC:DOPE:POPS), a dramatic absorption flatting of MAD1's CD signal is observed (FIG. 3a, black data). These changes can be attributed to the organization of peptide chromophores during their ordered interpolation within regions of high lipid density. This indicates that MAD1 is able to rapidly assemble within the cancer cell liposomal membrane to cause significant membrane destabilization and subsequent lysis, which is further corroborated by an increase in solution optical density (FIG. 3b) and the generation of macroscopic lipid fragments (FIG. 3b inset and FIG. 14). Conversely, MAD1 did not lyse the healthy liposomal counterparts.

DAP1, on the other hand, evolves from an ensemble of random coil conformations to a CD spectrum indicative of β-sheet rich and tryptophan stacked conformations in the presence of both normal and cancer cell membranes, as indicated by ellipticity minima at 212 and 230 nm, respectively (FIG. 3c). Parallel optical density measurements demonstrate that DAP1 exhibits a transient interaction with cancer cell membranes, leading to a temporary increase in optical density (FIG. 3d). Yet, DAP1 does not completely lyse cancer liposomes, as evidenced by rapid restoration of optical density back to baseline (FIG. 3d) and the absence of large lipid flocculates in solution (FIG. 14). This temporary turbidity change may be explained by transitory adsorption of the peptide to the lipid surface, or integration of the sequence into the bilayer to form stable peptide-lipid complexes without causing membrane lysis (FIG. 3d). Interestingly, DAP1 showed little interaction affinity with non-cancerous liposomes, despite eliciting potent toxicity towards healthy cells lines tested in our in vitro assays (Table 2). This suggests these highly simplified liposomal membrane models may be missing other factors that influence ACP activity and specificity, including sphingolipids, cholesterol and surface glycans; the latter particularly influential on ACP potency.

Collectively, the described biophysical data suggests that MAD1 preferentially interpolates into the membranes of cancer cells to elicit selective oncolytic activity. The supramolecular assembly of DAP1, conversely, appears to poorly discriminate healthy from cancerous membranes (FIG. 3c), providing further mechanistic insight into the differential cell cytotoxicity profiles of the two peptides (Table 2).

EXAMPLE 4

MAD1 Mechanism of Action

Figure 4:
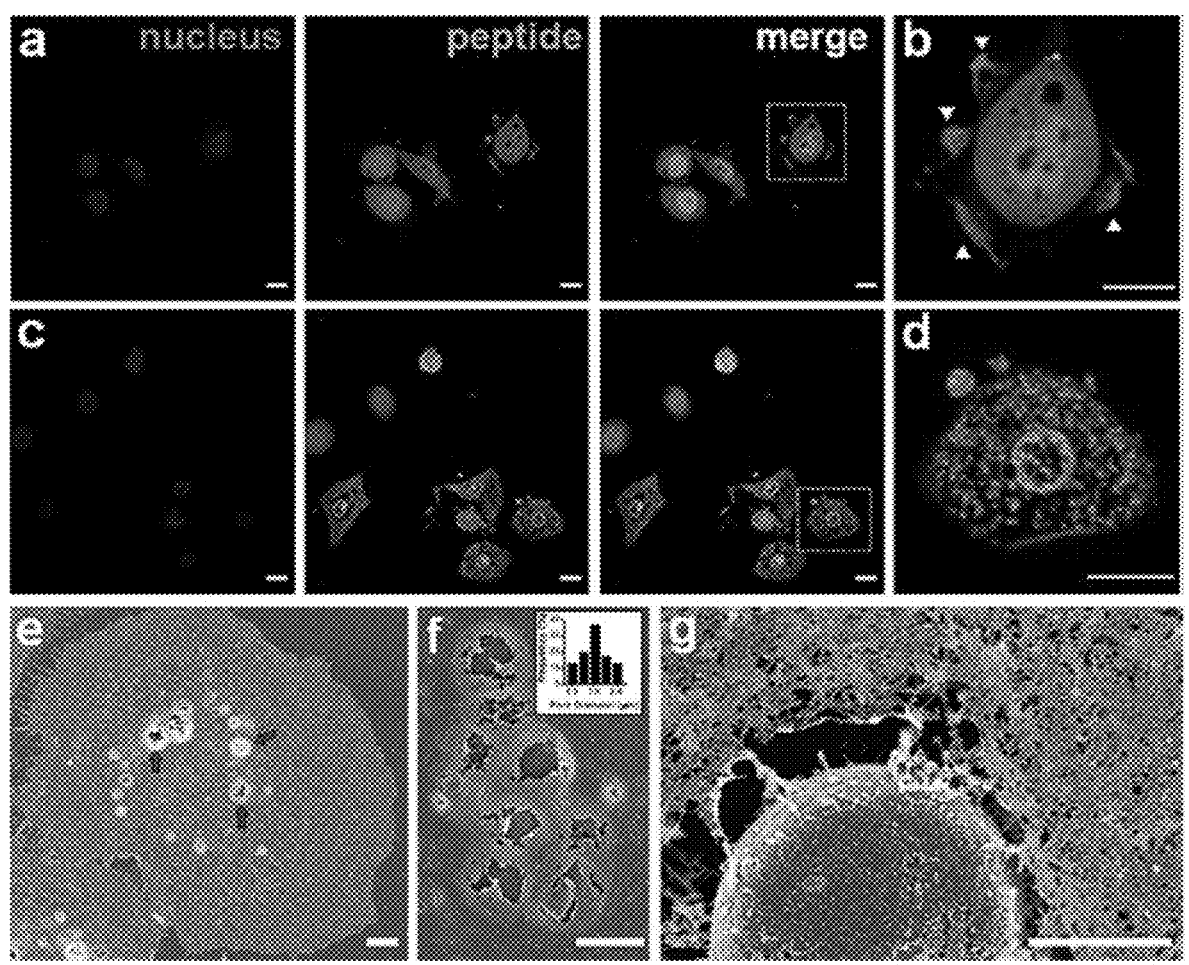
FIG. 4. MAD1 integration into cancer cells and subcellular trafficking. (a) Confocal micrographs of OVCAR-3 ovarian carcinoma cells treated with 14 µM of fluorescein-labeled MAD1 for 1 hour. (b) Magnification of boxed cell in merged image of panel a. Membrane ruffling marked by white arrows. (c) Micrographs of OVCAR-3 cells following a 10 hour incubation with MAD1. (d) Magnification of boxed cell in merged image of panel c demonstrating peptide localization to the nuclear envelope (see FIG. 15 for 3D z-stacks). Scale bars for panels a-d=15 µm. (e) SEM image of membrane-templated MAD1 pores following a 1 hour treatment of OVCAR-3 cells with MAD1. Peptide-induced surface pores highlighted by red arrows. (f) Magnification of membrane pores formed by MAD1. Inset: Histogram of pore diameter. (g) Magnified SEM micrograph of an OVCAR-3 cell treated for 4 hours with MAD1 (full image can be found in FIG. 17). Cell membrane (orange) and nucleus (blue) have been false-colored to aid visualization. Scale bar for panels e-g=5 µm.
Figure 5:
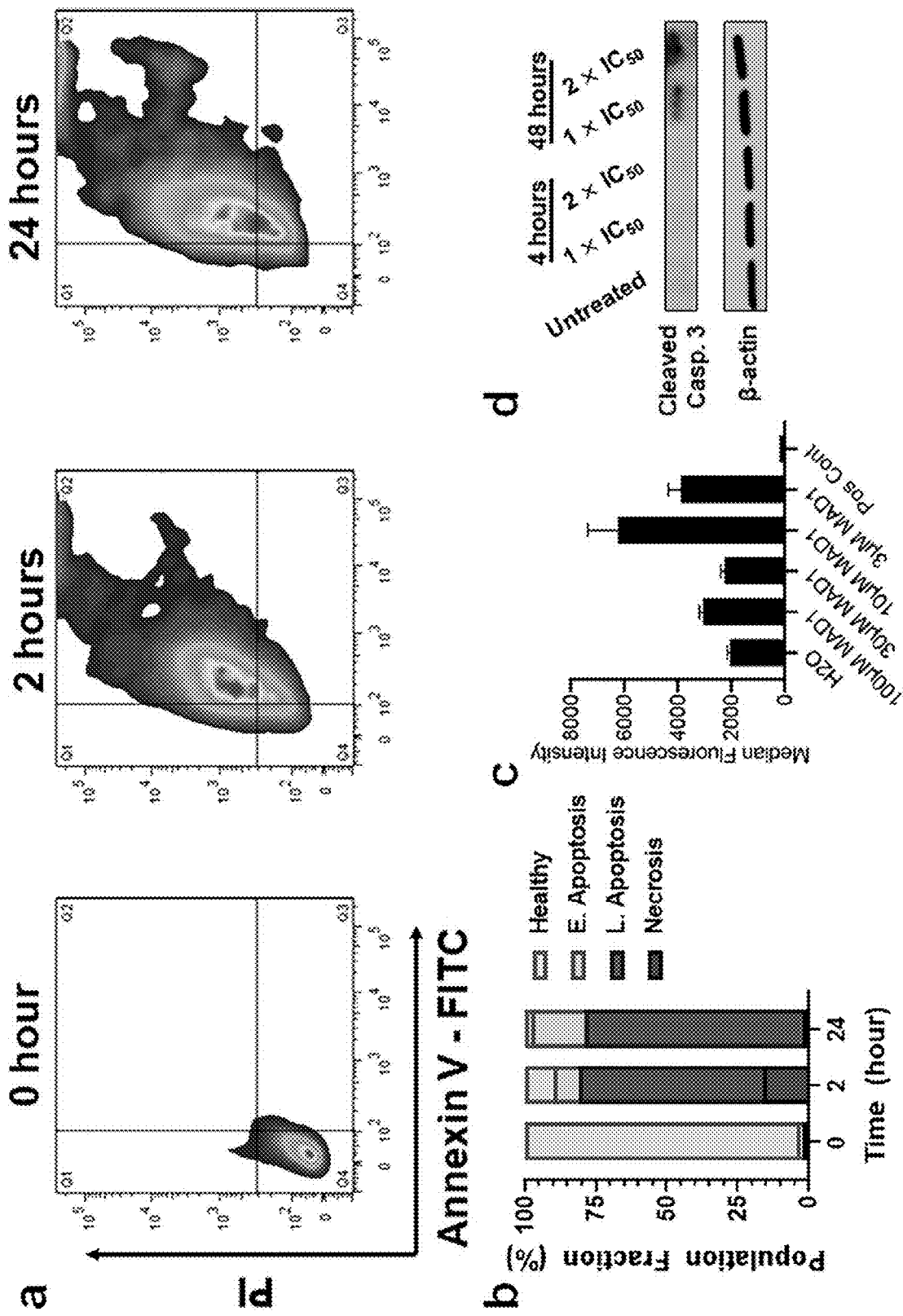
FIG. 5. Mechanism of antitumor action by MAD1. (a) Representative plots from flow cytometric PI/Annexin V-FITC apoptosis assays of OVCAR-3 cells treated with 14 µM of MAD1 for 2 or 24 hours. (b) Quadrant quantification of flow cytometry data defining the healthy cell population from necrotic cells, or those in early and late apoptosis, as a function of incubation time with the peptide. (c) Quantification of TMRE fluorescence for OVCAR-3 cells treated with varying concentrations of MAD1. Water or FCCP were included as a negative and positive control, respectively. (d) Western blot analysis of cleaved caspase 3 from OVCAR-3 cells after incubation with medium alone (untreated), or MAD1 at 1× and 2× its $IC_{50}$ for 4 and 48 hours.
Figure 15:
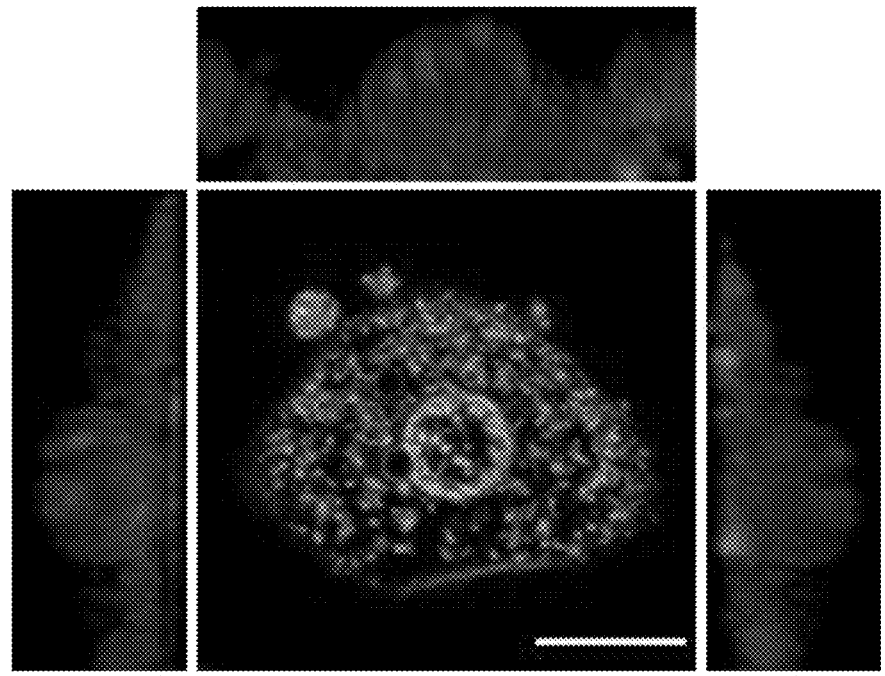
FIG. 15. 2D confocal image, and orthogonal 3D z-stacks, of OVCAR-3 cells after a 10 hour treatment with fluorescently-labeled MAD1 peptide. Scale bar=15 µm.
Figure 16:
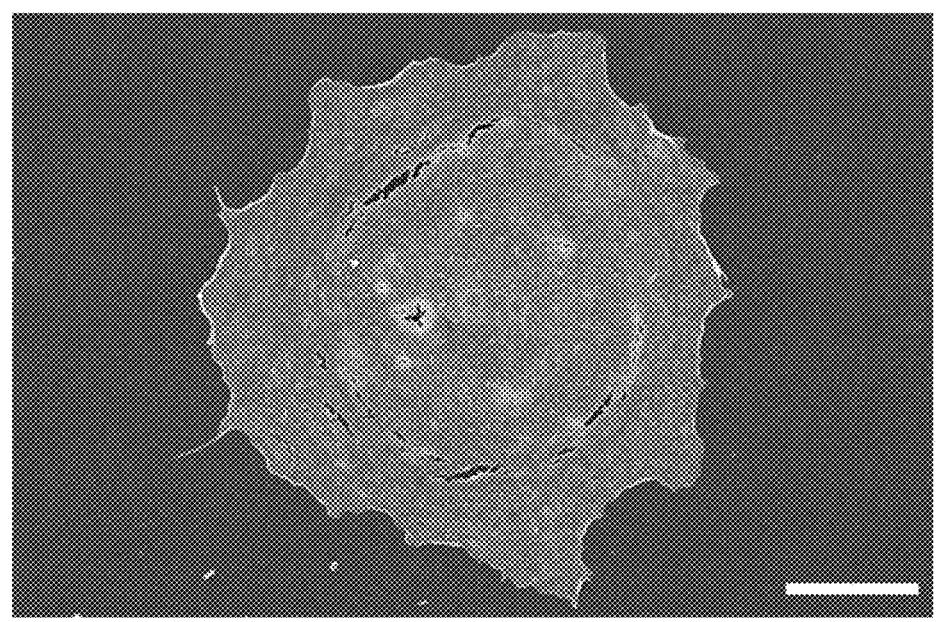
FIG. 16. SEM image of an untreated OVCAR-3 cell. Scale bar=15 µm
Figure 17:
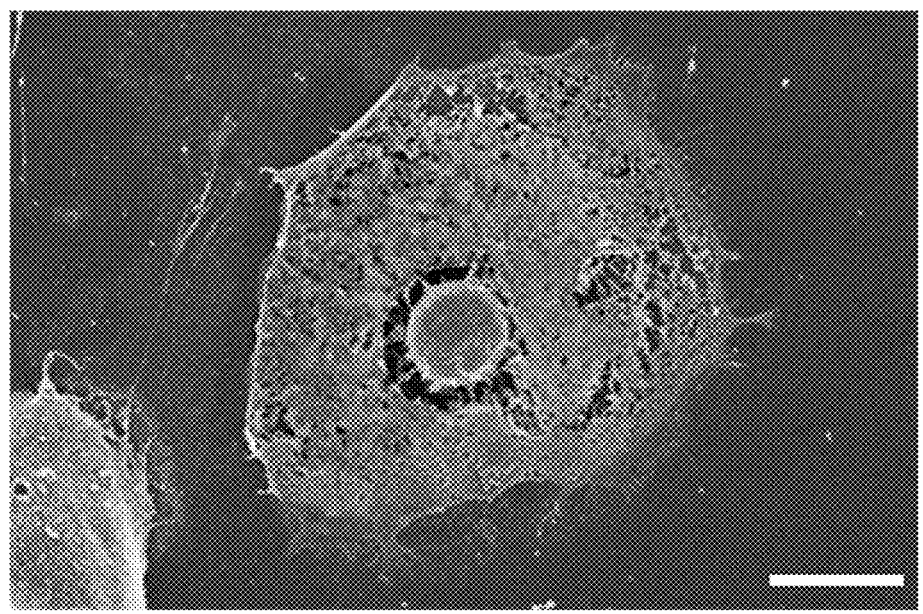
FIG. 17. SEM image of an OVCAR-3 cell treated with MAD1 for 4 hours. Scale bar=15 µm.
Figure 18:
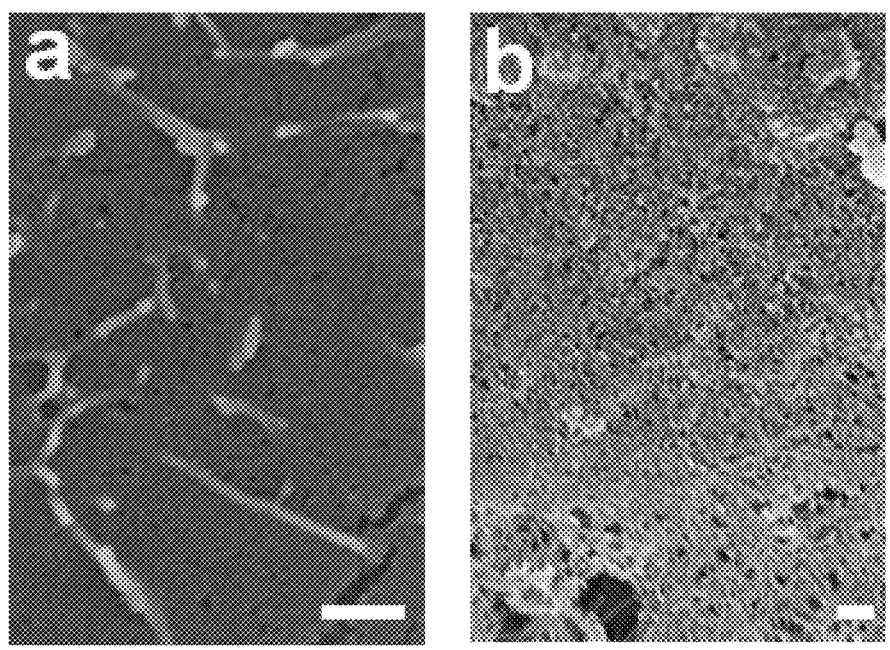
FIG. 18. SEM image of OVCAR-3 cell surface topography for (a) untreated controls, or (b) cells treated with MAD1 for 4 hours. Gross changes in surface morphology, as well as the loss of glycan filaments, is observed following treatment with MAD1. Scale bar=100 nm.
Figure 19:
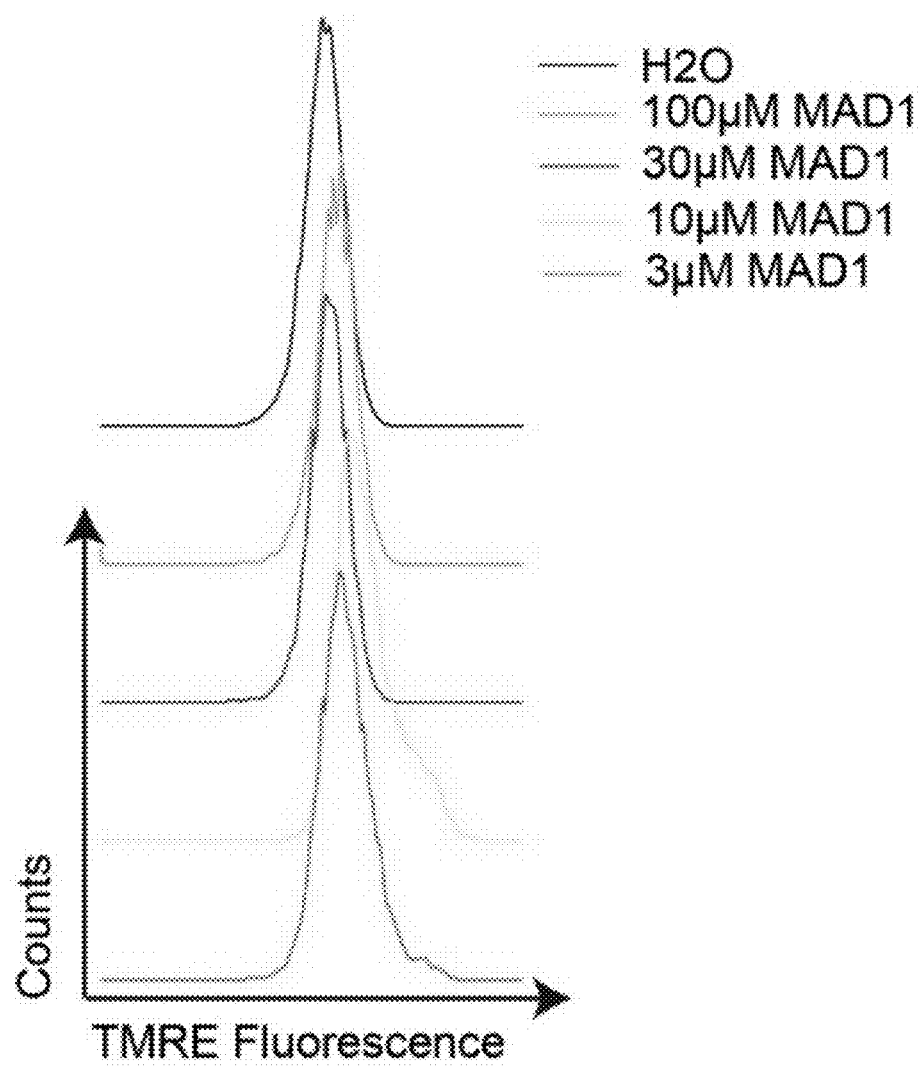
FIG. 19. Flow cytometric analysis of OVCAR-3 cells labeled with TMRE and treated in the absence ($H_2O$) or presence of the MAD1 peptide at varying concentrations.

Recent studies suggest that many ACPs exploit diverse physical (lytic) and biochemical (apoptotic) modes of toxicity, which operate in either an independent or coincident fashion depending on the cell type. This is exemplified in the present disclosure, in which DAP1 displayed similar potency across all cell lines tested, whereas MAD1 demonstrated a strong preference for OVCAR-3 ovarian carcinoma cells (Table 2). Thus, DAP1 may employ a cell-type agnostic mechanism, while MAD1 potentially elicits a combination of necrosis and apoptosis that is particularly potent towards ovarian carcinomas. To investigate this, we monitored the time-dependent subcellular localization of a fluorescently-labeled MAD1 analogue in OVCAR-3 cells (FIG. 4a). Results show that, shortly after addition, MAD1 decorates the surfaces of treated ovarian cancer cells. Interestingly, exposure of OVCAR-3 to MAD1 evoked a ruffled morphology of the cellular surface, particularly at the migratory leading edges (FIG. 4b). This is complemented by the appearance of micron-sized defects in the plasma membrane. After this initial surface binding, MAD1 translocates to the cytoplasm (FIG. 4c) and subsequently localizes to the nuclear envelope (FIG. 4d, FIG. 15). To confirm these observations, as well as directly visualize MAD1-induced damage to the plasma and nuclear membranes, we performed scanning electron microscopy. SEM imaging at 1 hour after peptide addition confirms that MAD1 rapidly assembles within the membranes of cancer cells to form micron-sized pores (FIG. 4e, see untreated control in FIG. 16), with an average diameter of ~1.5 µm (FIG. 4f). This is followed later by peptide-mediated degradation of the nuclear envelope (FIG. 4g, FIG. 17), as well as significant morphologic changes to membrane nano-topography (FIG. 18). Although ACP-mediated damage to plasma and mitochondrial membranes has been observed previously, to our knowledge MAD1 is the first example of an amphipathic peptide with the capacity to preferentially bind and disrupt the nuclear envelope. Taken together, this suggests that insertion and supramolecular assembly of MAD1 within the membranes of cancer cells alters bilayer tension and destabilizes the protective nuclear enclosure. Accordingly, this may lead to the induction of apoptotic signaling cascades after initial necrotic priming of cancer cells by the peptide. To test this, we performed annexin V-PI flow cytometry assays following treatment of OVCAR-3 cells at the $IC_{50}$ of MAD1 for 2 and 24 hours (FIG. 5a). Results show that, although MAD1 causes considerable cell necrosis (16% of population) at early time points (2 hours), the majority of cells (65%) adopt a late apoptotic phenotype (FIG. 5b). After 24 hours cells predominantly occupy early (19%) and late (77%) apoptotic stages. This rapid induction of apoptosis may be caused by mitochondrial depolarization, which can activate caspase cascades within 30 minutes. To investigate this, we utilized a TMRE-staining flow cytometry assay to evaluate mitochondrial transmembrane potential in OVCAR-3 cells after a 48 hour incubation with the peptide. Here, intact mitochondria take up the TMRE dye and brightly fluoresce, while depolarized or inactive mitochondria fail to sequester the TMRE fluorophore. Results in FIG. 5c and FIG. 19 show that OVCAR-3 mitochondrial integrity is generally unchanged in the presence of MAD1, and at certain peptide concentrations appears to increase. This indicates that MAD1 does not affect mitochondrial activity to potentiate intrinsic apoptotic signaling in treated cancer cells. Yet, parallel western blot experiments confirm the presence of cleaved caspase 3, a common effector of both intrinsic and extrinsic apoptotic pathways, in MAD1-treated OVCAR-3 cells (FIG. 5d). Taken together, this indicates that MAD1's early lytic effects are complemented later by the induction of extrinsic apoptotic pathways. Given that the peptide assembles at the surfaces of cancer cells (FIG. 4), the most likely explanation for this is that membrane-templated supramolecular assembly of MAD1 leads to ligation of extrinsic FAS, TNF or TRAIL death receptors.

However, our western blot data, which demonstrates that MAD1-mediated activation of caspase 3 does not occur until 48 hours, contradicts the annexin V-PI assays which show that the peptide induces apoptosis within 2 hours (FIGS. 5a and b). Without intending to be bound by any particular theory, one explanation for these results in that early MAD1-mediated poration of the cancer cell plasma membrane allows the cytosolic diffusion of the otherwise cell-impermeant annexin-V probe, which can then bind its phosphatidylserine lipid target on the inner leaflet. An alternative is that membrane interpolation of MAD1 rearranges lipids in the asymmetric bilayer and physically translocates phosphatidylserine to the outer leaflet, where it then binds the annexin-V protein. In both scenarios MAD1 treated cells would stain positive for apoptosis at these early time points, but ultimately experience an oncolytic mechanism.

EXAMPLE 5

Anticancer Synergy

Figure 6:
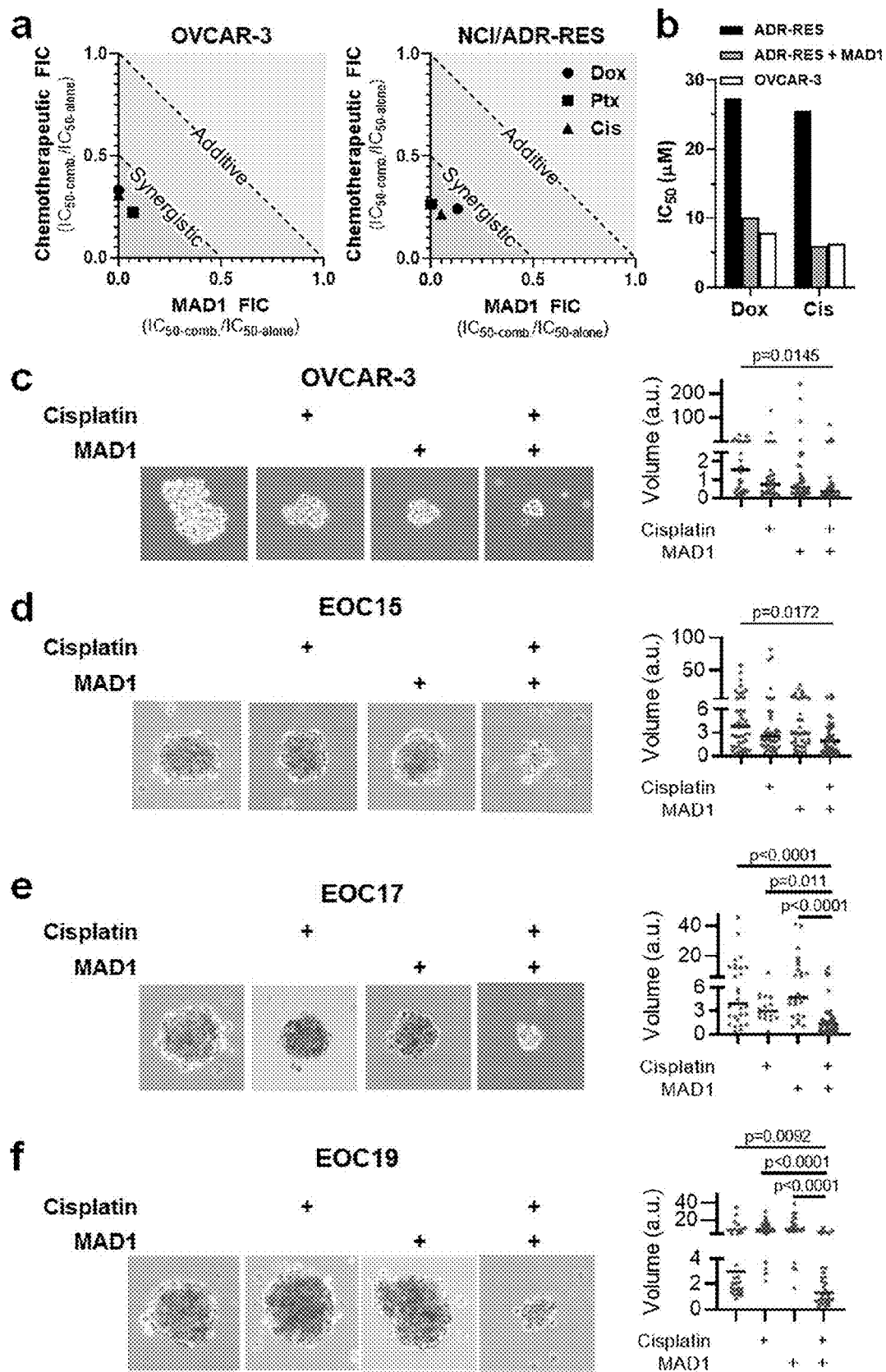
FIG. 6. Chemotherapeutic synergy. (a) Isobolograms of MAD1 and Doxorubicin (Dox), Paclitaxel (Ptx) or Cisplatin (Cis) combinatorial synergy in OVCAR-3 (left) and NCI/ADR-RES (right) cells. Fractional inhibitory concentration (FIC) <1 and <0.5 represent additive and synergistic effects, respectively. (b) Comparison of Dox and Cis $IC_{50}$ towards NCI/ADR-RES as either a monotherapy (ADR-RES, black) or in combination with 20 µM MAD1 (ADR-RES+MAD1, grey). Activity of each drug as a monotherapy in pre-resistant OVCAR-3 (OVCAR-3, white) cells shown for comparison. (c-f) Indicated ovarian cancer cell line or patient-derived ovarian carcinoma cells were cultured in ultra-low attachment conditions and treated for 48 hours with 2 µM cisplatin or 4 µM MAD1 alone and in combination. Data represent volume in arbitrary units (a.u.) and median.
Figure 7:
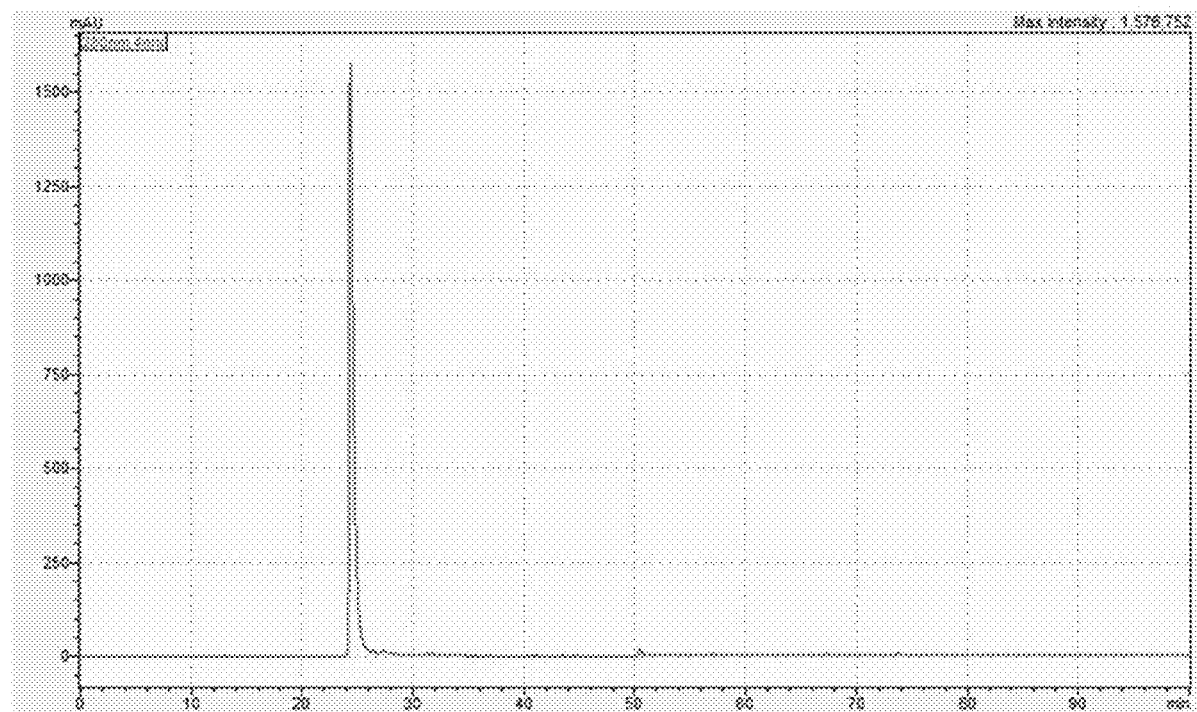
FIG. 7. Top: Analytical HPLC chromatogram (Luna Omega C18 column, linear gradient of 0-100% solvent B over 100 minutes) and Bottom: ESI (+) mass spectrum of purified MAD1 with calculated and observed masses reported.
Figure 7:
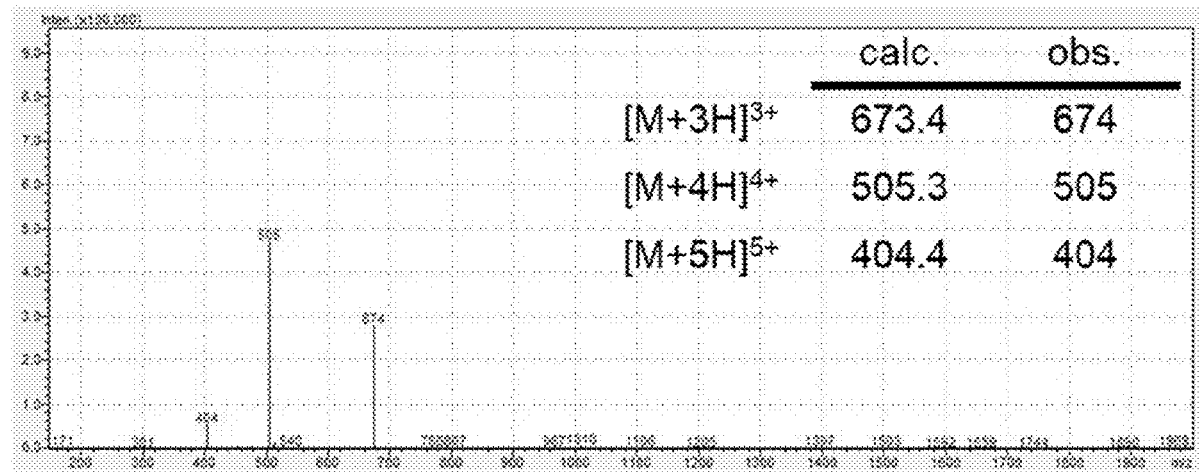
Figure 8:
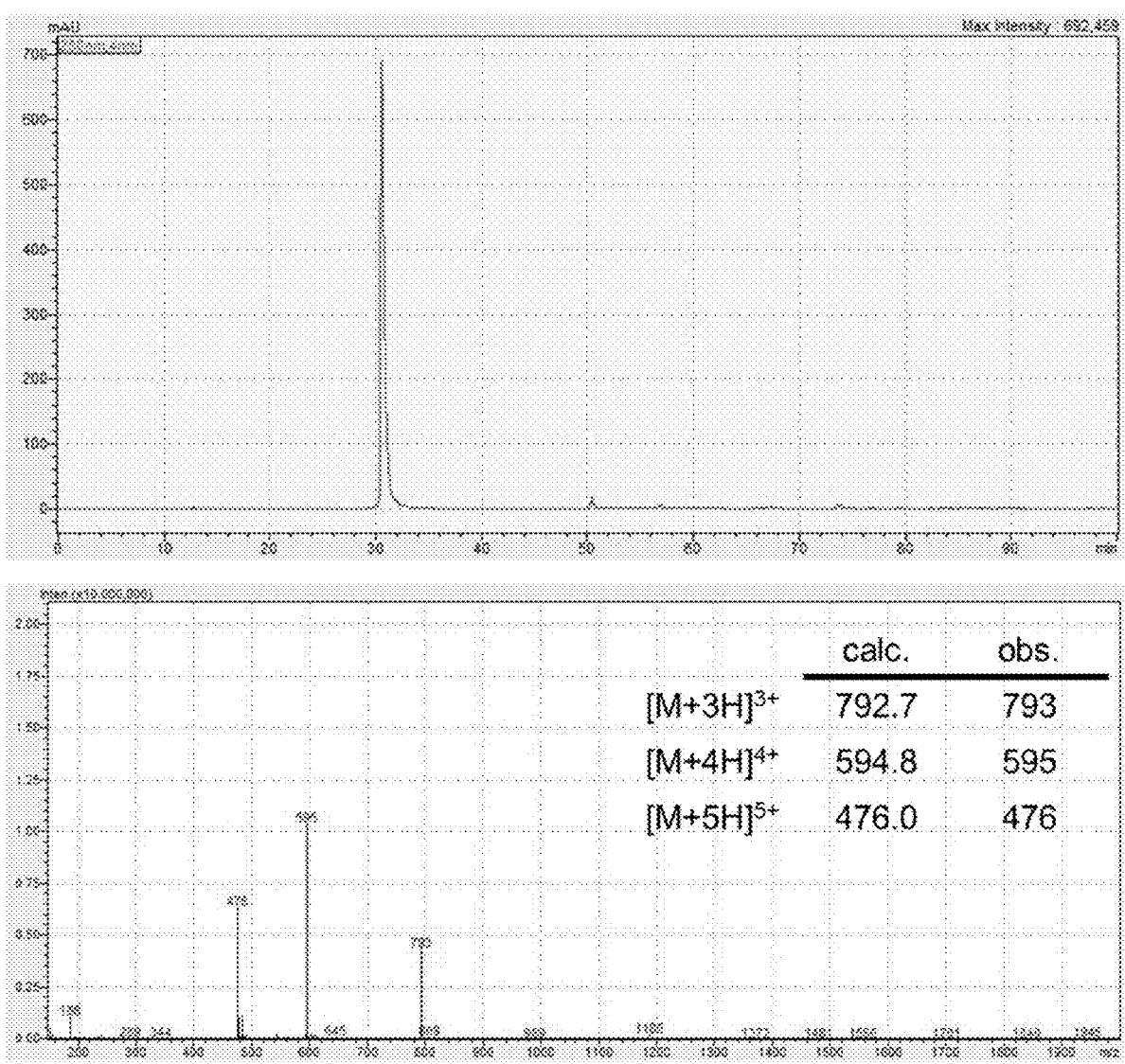
FIG. 8. Top: Analytical HPLC chromatogram (Luna Omega C18 column, linear gradient of 0-100% solvent B over 100 minutes) and Bottom: ESI (+) mass spectrum of purified FITC-MAD1 with calculated and observed masses reported.
Figure 9:
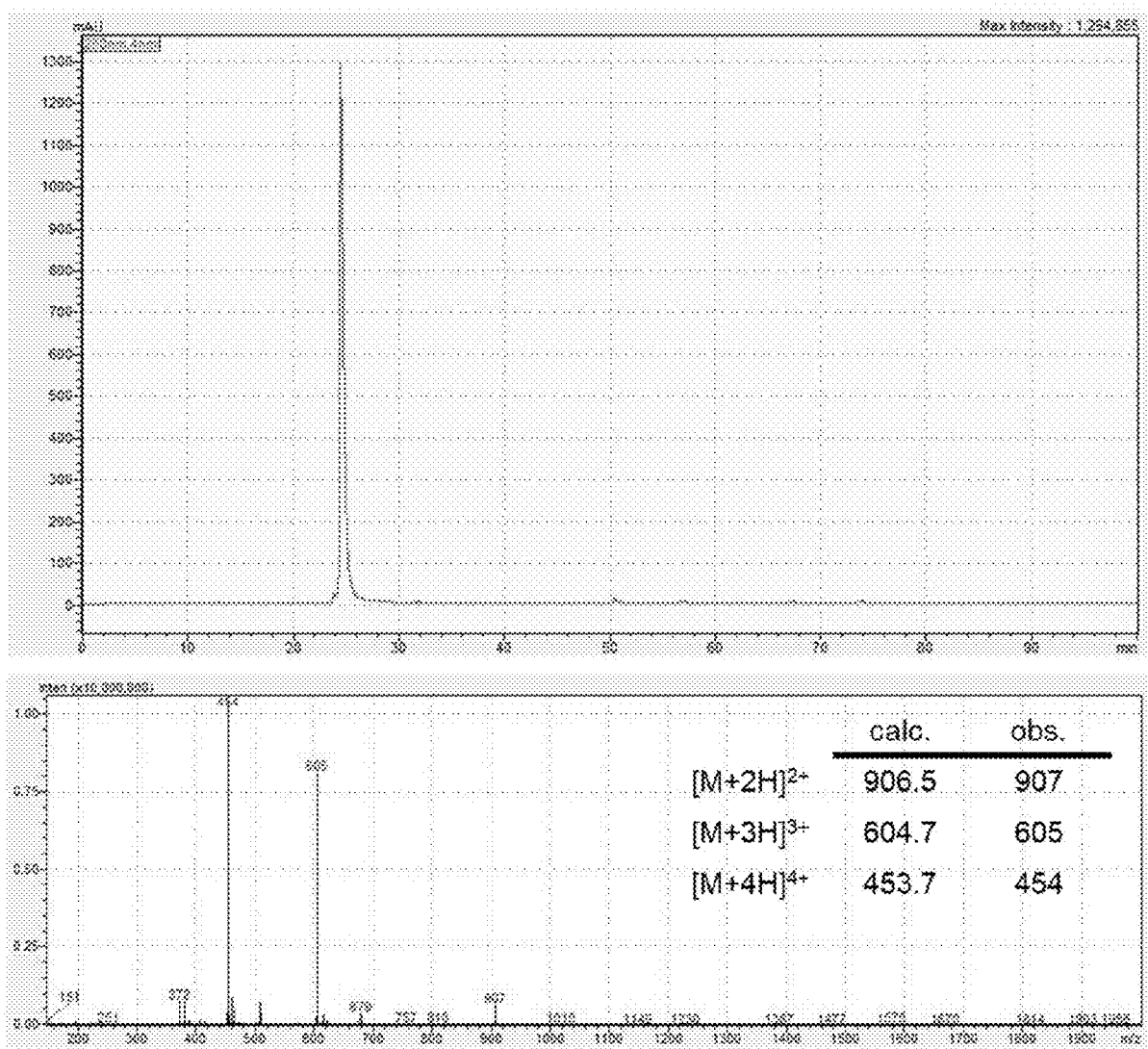
FIG. 9. Top: Analytical HPLC chromatogram (Luna Omega C18 column, linear gradient of 0-100% solvent B over 100 minutes) and Bottom: ESI (+) mass spectrum of purified DAP1 with calculated and observed masses reported.
Figure 10:
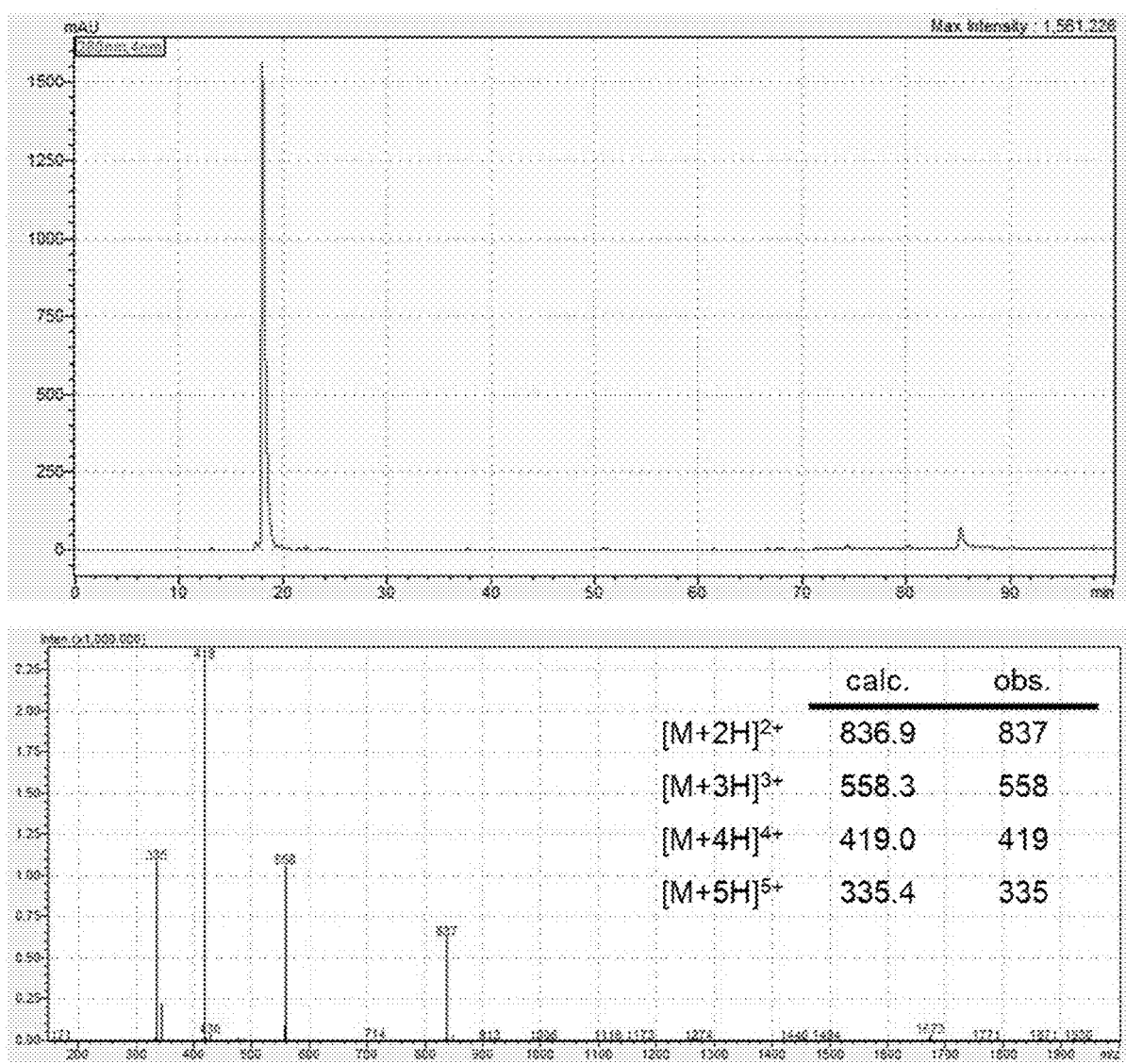
FIG. 10. Top: Analytical HPLC chromatogram (Luna Omega C18 column, linear gradient of 0-100% solvent B over 100 minutes) and Bottom: ESI (+) mass spectrum of purified DAP2 with calculated and observed masses reported.
Figure 20:
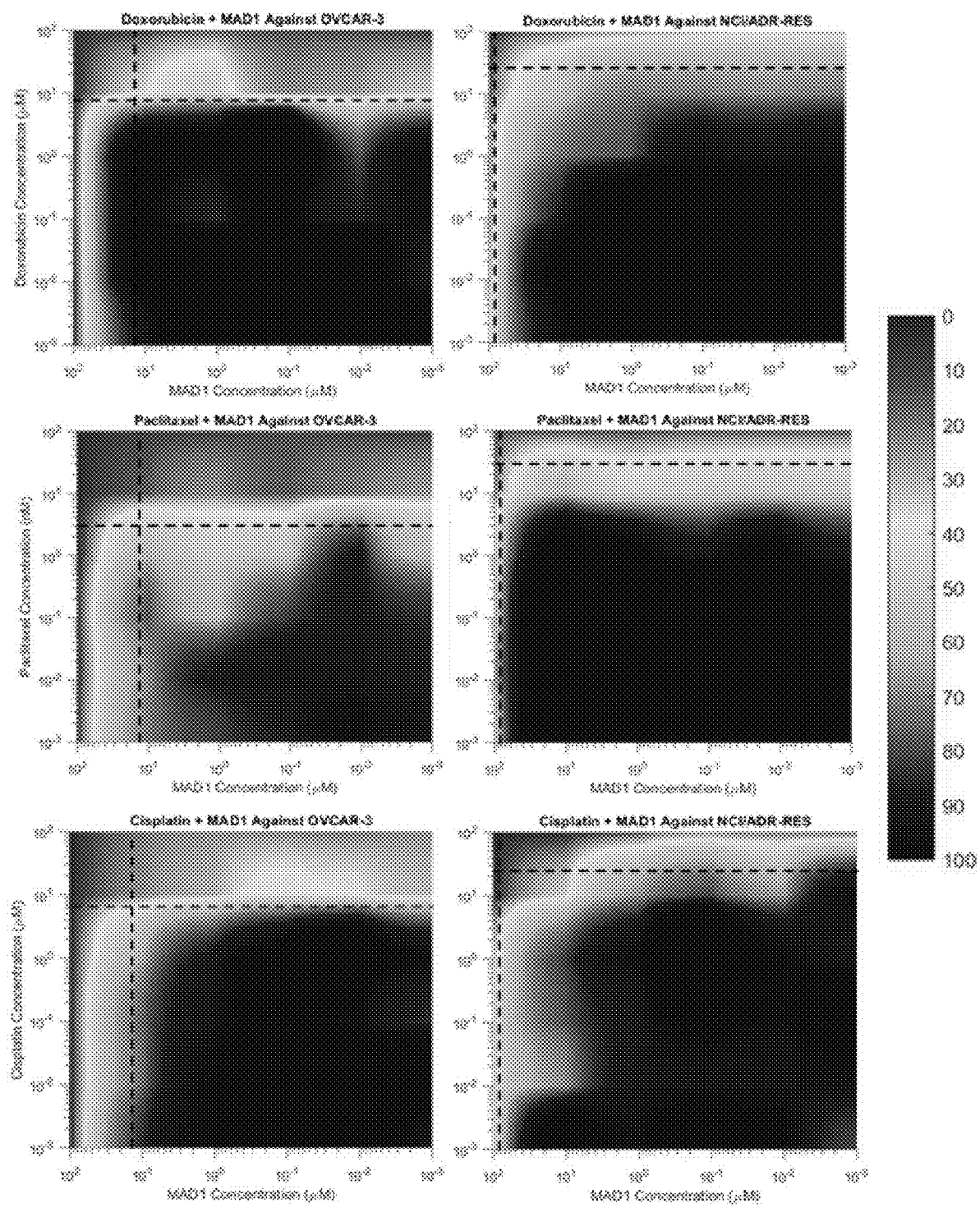
FIG. 20. Heat map of MAD1 and listed drug combinatorial cytotoxicity towards OVCAR-3 and NCI/ADR-RES cell lines. Color legend represents 100% (blue) to 0% (red) cell viability. Dashed lines represent the individual $IC_{50}$ of each compound in the tested cell line.
Figure 21:
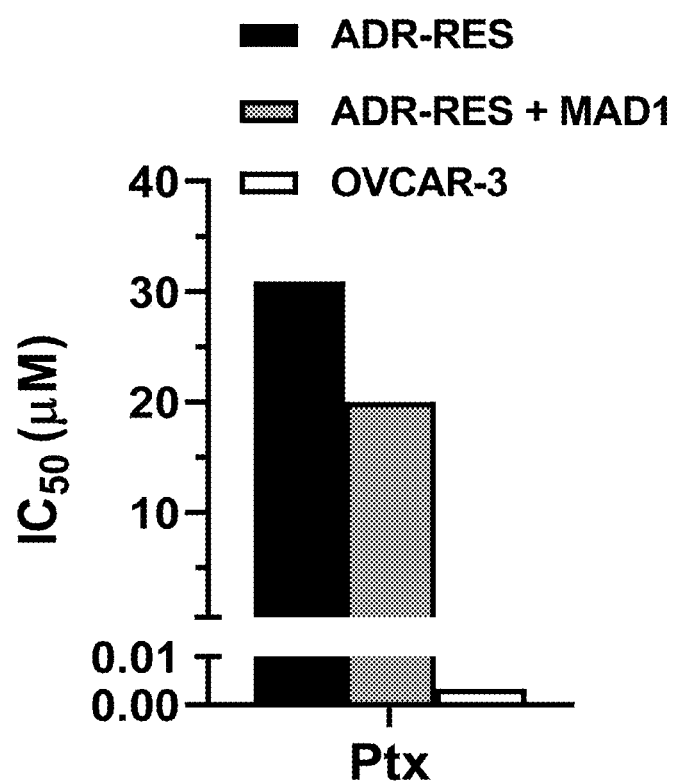
FIG. 21. Comparison of Ptx $IC_{50}$ towards NCI/ADR-RES, NCI/ADR-RES cells co-treated with 20 µM MAD1, or the pre-resistant OVCAR-3 line.

Given MAD1's selective action against ovarian cancer cells, and its co-induction of physical (lysis) and biochemical (extrinsic apoptosis) death pathways, we next tested its potential to synergistically enhance the potency of three chemotherapeutics commonly used to treat ovarian carcinomas: Doxorubicin (Dox), Paclitaxel (Ptx) and Cisplatin (Cis). Remarkably, in both drug-refractory (OVCAR-3) and multidrug resistant (NCI/ADR-RES) ovarian cancer lines MAD1 potently synergizes with all three therapeutics tested (FIG. 6a, Suppl. Table 1 and FIG. 20). As a notable example, co-treatment of multidrug resistant NCI/ADR-RES cells in the presence of 20 μM MAD1 restored the potency of both Dox and Cis to a level equivalent to the more sensitive OVCAR-3 cell line (FIG. 6b, analysis derived from combinatorial heat maps shown in FIG. 21). Conversely, Paclitaxel showed only a modest improvement in potency when combined with 20 μM MAD1 (FIG. 21).

Clinically, late-stage epithelial ovarian cancer (EOC) is characterized by dissemination of the disease into the peritoneal cavity to form tumor spheroids, which is then typically treated with platinum-based chemotherapy (e.g. Cisplatin). In order to mimic these conditions ex vivo, ultra-low attachment culture plates were used to induce the formation of 3D tumor spheroids using OVCAR-3 cells, as well as three patient-derived lines (EOC15, 17, 19), which were then treated alone or in combination with Cisplatin and/or MAD1 (FIG. 6c-f). Remarkably, all three patient-derived tumor cell spheroids showed minimal reduction in size when treated with either Cisplatin or MAD1 alone, while the combination produced potent and synergistic anticancer effects. These ex vivo studies confirm that MAD1 synergizes with platinum-based drugs to decrease ovarian cancer cell size, even in advanced patient-derived carcinomas that are often refractory to the standard of care.

It will be recognized from the foregoing that the described peptides represent anticancer agents that do not target a resistance-susceptible biochemical pathway, but instead act by physically disrupting key structural elements, including the plasma and nuclear membrane, that are difficult for cancer cells to mutationally alter. As an exemplary application, the disclosure demonstrates that MAD1 can be repurposed as a potent ovarian cancer targeting ACP. Surprisingly, this peptide displays an unusual specificity for human ovarian carcinomas and synergistically enhances the activity of clinical therapies towards drug-refractory and -resistant tumors. This is particularly impactful as many ovarian cancer patients are diagnosed at an advanced stage, and either relapse or succumb to the disease as a result of chemotherapeutic resistance.

TABLE 1

Sequence and physiochemical properties of de novo designed ACPs

| Peptide | Sequence[a] | Sequence Length | Formal Charge[b] | logD | Hydrophobic Moment |
|---|---|---|---|---|---|
| MAD1 | KRWHWWR RHWWW-NH$_2$ (SEQ ID NO: 1) | 13 | +7 | −3.41 | 14.828 |
| DAP1 | LWKRWVG VWRKWL-NH$_2$ (SEQ ID NO: 2) | 13 | +5 | −3.23 | 13.879 |
| DAP2 | RWGKWFK KNSHLS-NH$_2$ (SEQ ID NO: 3) | 13 | +5 | −9.37 | 15.250 |
| AMP1 | WKWLKKW IK-NH$_2$ (SEQ ID NO: 4) | 9 | +4 | −6.46 | 13.449 |
| AMP2 | KRWWKWW RR-NH$_2$ (SEQ ID NO: 5) | 9 | +5 | −6.90 | 15.084 |

[a]All peptides are prepared with amidated C-terminus
[b]Formal charge includes N-terminal amine. Histidine considered partially protonated for purposes of formal charge calculation.

TABLE 2

Peptide cytotoxicity towards cancerous and non-cancerous cell lines

| | Cancerous (IC$_{50}$, μM) | | | | Healthy (IC$_{50}$, μM) | | Therapeutic Index[a] | | | |
|---|---|---|---|---|---|---|---|---|---|---|
| Peptide | A549 | OVCAR-3 | NCI/ADR-RES | T24 | HUVEC | NL20 | A549 | OVCAR-3 | NCI/ADR-RES | T24 |
| MAD1 | 36.2 | 14.2 | 85.6 | >100 | >100 | 76.9 | 2.8 | 7.0 | 1.2 | — |
| DAP1 | 11.9 | 8.6 | 14.0 | 15.3 | 19.5 | 19.0 | 1.6 | 2.3 | 1.4 | 1.3 |
| DAP2 | >100 | >100 | >100 | >100 | >100 | >100 | — | — | — | — |
| AMP1 | — | 51.1 | — | — | — | — | — | — | — | — |
| AMP2 | — | 53.5 | — | — | — | — | — | — | — | — |

[a]Therapeutic index of each peptide for indicated cell type relative to HUVEC controls (IC$_{50\text{-}HUVEC}$/IC$_{50\text{-}indicated\ cell}$)

TABLE 3

Minimum inhibitory concentration (MIC) of de novo ACPs

| | | MIC (μM) | | |
|---|---|---|---|---|
| | Bacteria | MAD1 | DAP1 | DAP2 |
| Gram Positive | B. subtilis (168) | 0.2 | <0.6 | >80 |
| | MS S. aureus | >80[a] | 7 | >80 |
| | MR S. aureus | >80[a] | 5 | >80 |
| Gram Negative | P. aeruginosa | 50[a] | 20 | >80 |
| | E. coli | 25 | 10 | >80 |
| Mycobacteria | M. tuberculosis | 2.5 | 20 | >80 |

SUPPL. TABLE 1

FIC of MAD1 and chemotherapeutics

| | Combined FIC Score | | |
|---|---|---|---|
| Cell Line | Dox | Ptx | Cis |
| OVCAR-3 | 0.33 | 0.30 | 0.31 |
| NCI/ADR-RES | 0.37 | 0.27 | 0.27 |

While the disclosure has been illustrated by the foregoing description, the described invention is intended to include variations and modifications that will be apparent to those skilled in the art when given the benefit of the present description and figures.

What is claimed is:

1. A method for inhibiting growth of cancer in an individual in need thereof, the method comprising administering to the individual an effective amount of a peptide comprising KRWHWWRRHWVVW-NH$_2$ (SEQ ID NO:1) to thereby inhibit the growth of the cancer, wherein the cancer is lung cancer, bladder cancer, or ovarian cancer.

2. The method of claim 1, further comprising administering sequentially or concurrently a chemotherapeutic agent to the individual, wherein the peptide and the chemotherapeutic agent act synergistically to inhibit growth of the cancer in the individual, and wherein optionally the cancer in the individual is resistant to the chemotherapeutic agent in the absence of administration of the peptide.

3. The method of claim 1, wherein the cancer is ovarian cancer.

4. The method of claim 1, wherein the cancer is lung cancer.

5. The method of claim 1, wherein the cancer is bladder cancer.

* * * * *

```
                        SEQUENCE LISTING

<160> NUMBER OF SEQ ID NOS: 5

<210> SEQ ID NO 1
<211> LENGTH: 13
<212> TYPE: PRT
<213> ORGANISM: artificial sequence
<220> FEATURE:
<223> OTHER INFORMATION: antimicrobial peptide

<400> SEQUENCE: 1

Lys Arg Trp His Trp Trp Arg Arg His Trp Val Val Trp
1               5                   10

<210> SEQ ID NO 2
<211> LENGTH: 13
<212> TYPE: PRT
<213> ORGANISM: artificial sequence
<220> FEATURE:
<223> OTHER INFORMATION: antimicrobial peptide

<400> SEQUENCE: 2

Leu Trp Lys Arg Trp Val Gly Val Trp Arg Lys Trp Leu
1               5                   10

<210> SEQ ID NO 3
<211> LENGTH: 13
<212> TYPE: PRT
<213> ORGANISM: artificial sequence
<220> FEATURE:
<223> OTHER INFORMATION: antimicrobial peptide

<400> SEQUENCE: 3

Arg Trp Gly Lys Trp Phe Lys Lys Asn Ser His Leu Ser
1               5                   10
```

```
<210> SEQ ID NO 4
<211> LENGTH: 9
<212> TYPE: PRT
<213> ORGANISM: artificial sequence
<220> FEATURE:
<223> OTHER INFORMATION: antimicrobial peptide

<400> SEQUENCE: 4

Trp Lys Trp Leu Lys Lys Trp Ile Lys
1               5

<210> SEQ ID NO 5
<211> LENGTH: 9
<212> TYPE: PRT
<213> ORGANISM: artificial sequence
<220> FEATURE:
<223> OTHER INFORMATION: antimicrobial peptide

<400> SEQUENCE: 5

Lys Arg Trp Trp Lys Trp Trp Arg Arg
1               5
```